United States Patent [19]

Tseng

[11] Patent Number: 4,786,316

[45] Date of Patent: Nov. 22, 1988

[54] HERBICIDAL ORTHO-SULFAMOYL SULFONAMIDES

[75] Inventor: Chi-Ping Tseng, Wilmington, Del.

[73] Assignee: E. I. Du Pont de Nemours and Company, Wilmington, Del.

[21] Appl. No.: 941,713

[22] Filed: Dec. 12, 1986

Related U.S. Application Data

[60] Division of Ser. No. 628,939, Jul. 13, 1984, Pat. No. 4,652,304, which is a continuation-in-part of Ser. No. 533,771, Sep. 19, 1983, abandoned.

[51] Int. Cl.$^4$ .................. C07D 251/52; C07D 403/12; A01N 43/66; A01N 43/70
[52] U.S. Cl. ........................................ 71/93; 544/113; 544/211; 544/212; 544/206; 544/207; 544/208; 544/209; 544/219
[58] Field of Search .................... 71/93; 544/113, 211, 544/212, 206, 207, 208, 209, 219

[56] References Cited

U.S. PATENT DOCUMENTS

| 4,310,346 | 1/1982 | Levitt et al. | 71/92 |
| 4,478,635 | 10/1984 | Meyer et al. | 71/92 |
| 4,551,531 | 11/1985 | Meyer et al. | 544/320 |
| 4,655,823 | 4/1987 | Shapiro | 71/93 |

FOREIGN PATENT DOCUMENTS 1689083  1/1984  Australia.

*Primary Examiner*—John M. Ford

[57] ABSTRACT

A class of ortho-sulfamoyl sulfonamides are useful as pre-emergent or post-emergent herbicides and plant growth regulants.

16 Claims, No Drawings

HERBICIDAL ORTHO-SULFAMOYL SULFONAMIDES

RELATED APPLICATION

This application is a divisional of my copending application U.S. Ser. No. 628,939, filed July 13, 1984, now U.S. Pat. No. 4,652,304, which in turn is a continuation-in-part of copending application U.S. Ser. No. 533,771 filed Sept. 19, 1983, now abandoned.

BACKGROUND OF THE INVENTION

The present invention relates to a class of ortho-sulfamoyl sulfonamides useful as pre-emergent or post-emergent herbicides and plant growth regulators.

U.S. Pat. No. 4,310,346 issued Jan. 12, 1982 to Levitt et al. discloses herbicidal sulfonylurea compounds of the following structure.

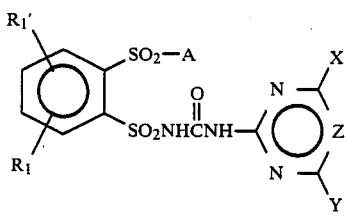

wherein, among other substituents, A can be $NR_2R_3$, $R_2$ can be H, $C_1-C_6$ alkyl, $R_3$ can be $C_1-C_4$ alkyl, and $NR_2R_3$ taken together can be

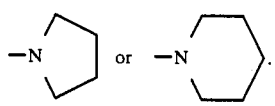

South African Patent Application No. 83/0127 teaches herbicidal N-arylsulfonyl-N'-pyrimidinylureas of formula

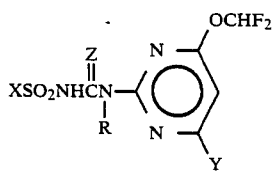

wherein X is optionally substituted phenyl or naphthyl.

SUMMARY OF THE INVENTION

This invention relates to novel compounds of Formula I, suitable agricultural compositions containing them and their method of use as pre-emergent or post-emergent herbicides or plant growth regulants.

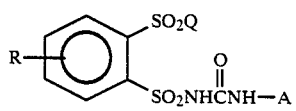

where
Q is $NR_1R_2$,

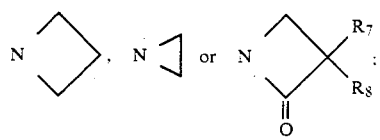

R is H, Cl, Br, F, $OCH_3$, $CH_3$ or $CF_3$;
$R_1$ is H, $C(O)R_3$, $C(O)NR_4R_5$, $CO_2R_6$ $C(O)NHR_9$ or $CF_2H$;
$R_2$ is H or $C_1-C_3$ alkyl;
$R_3$ is $C_1-C_4$ alkyl, $CF_3$ or aryl optionally substituted with Cl, $CH_3$, $CF_3$, $NO_2$ or $OCH_3$;
$R_4$ is H, $C_1-C_4$ alkyl or aryl optionally substituted with Cl, $CH_3$, $CF_3$, $NO_2$ or $OCH_3$;
$R_5$ is H or $C_1-C_4$ alkyl;
$R_4$ and $R_5$ may be taken together to be $-(CH_2)_4-$, $-(CH_2)_5-$ or $-CH_2CH_2OCH_2CH_2-$;
$R_6$ is $C_1-C_4$ alkyl;
$R_7$ and $R_8$ are independently H or $CH_3$;
$R_9$ is A-1;
A is

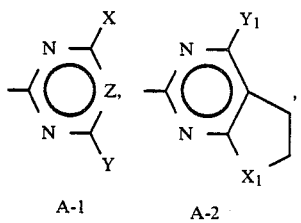

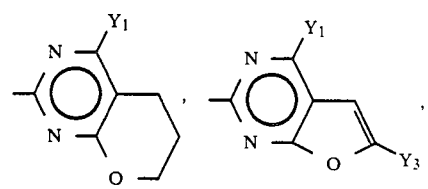

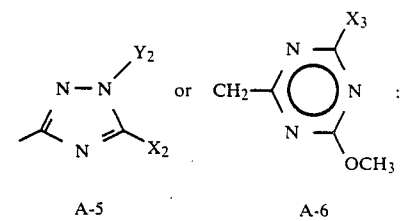

X is Cl, Br, $CH_3$, $CH_2CH_3$, $OCH_3$, $OCH_2CH_3$, $OCF_2H$ or $CF_3$;
Y is H, $NHCH_3$, $N(CH_3)_2$, $CH_3$, $CH_2CH_3$, $CF_3$, $OCH_3$, $OCH_2CH_3$, $CH_2F$, $CH_2OCH_3$, $CH_2OCH_2CH_3$, $OCH_2CH_2OCH_3$, $SCH_3$, $SCH_2CH_3$, $OCH_2CF_3$, $OCH_2CH_2F$, $OCH_2CH_2Br$, $OCH_2CH_2Cl$, $CH(OCH_3)_2$, $CH(OC_2H_5)_2$,

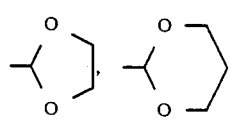

or $OCF_2H$;
Z is CH or N;
$X_1$ is O or $CH_2$;

$Y_1$ is H, $CH_3$, $OCH_3$ or Cl;
$X_2$ is $CH_3$, $OCH_3$ or $SCH_3$;
$Y_2$ is $CH_3$, $CH_2CH_3$ or $CH_2CF_3$;
$X_3$ is $CH_3$ or $OCH_3$; and
$Y_3$ is H or $CH_3$; and their agriculturally suitable salts; provided that (a) when $R_1$ is H, then $R_2$ must also be H;

(b) when $R_1$ is $CONHR_9$, then A must be A-1 and the values of X, Y and Z must be identical for both A and $R_9$;

(c) when X is Cl or Br, then Z is CH and Y is $NHCH_3$, $N(CH_3)_2$, $OCH_3$, $OCH_2CH_3$ or $OCF_2H$; and (d) when X or Y is $OCF_2H$ and Z is CH then $R_1$ must be other than H or $C(O)(C_1-C_3$ alkyl).

Preferred for their higher herbicidal activity, greater plant growth regulant activity and/or more favorable ease of synthesis are:

(1) Compounds of Formula I where R is H, A is A-1, X is $CH_3$, $CH_2CH_3$, $OCH_3$, $OCH_2CH_3$, Cl, $OCF_2H$ or $CF_3$ and Y is $CH_3$, $CH_2CH_3$, $OCH_3$, $OCH_2CH_3$, $CH_2OCH_3$, $CF_3$ or $CH(OCH_3)_2$;

(2) Compounds of Preferred 1 where Q is $NR_1R_2$ or

and $R_2$ is H or $CH_3$;

(3) Compounds of Preferred 2 where Q is $NR_1R_2$ or

, $R_1$ and $R_2$ are both H, X is $CH_3$, $OCH_3$ or Cl and Y is $CH_3$, $CH_2CH_3$, $OCH_3$, $OCH_2CH_3$ or $CH_2OCH_3$.

Exemplary compounds within the scope of the invention include:

N-[(4,6-Diemthoxypyrimidin-2-yl)aminocarbonyl]-1,2-benzenedisulfonamide, m.p. 192°–195° C. (d);

N-[(4-Methoxy-6-methylpyrimidin-2-yl)aminocarbonyl]-1,2-benzenedisulfonamide, m.p. 154°–155° C. (d);

2-(Azetidin-1-ylsulfonyl)-N-[(4,6-dimethoxy-1,3,5-triazin-2-yl)aminocarbonyl]benzenesulfonamide, m.p. 175°–177° C.;

2-(Azetidin-1-ylsulfonyl)-N-[(4-methoxy-6-methylpyrimidin-2-yl)aminocarbonyl]benzenesulfonamide, m.p. 220°–221° C. (d); and N,N'-bis-[(4,6-Dimethoxypyrimidin-2-yl)aminocarbonyl]-1,2-benzenedisulfonamide, m.p. 201°–203° C.; and 2-(Azetidin-1-yl-sulfonyl)-N-[(4-methoxy-6-methyl-1,3,5-triazin-2-yl)aminocarbonyl]benzenesulfonamide, m.p. 201° C.

DETAILED DESCRIPTION OF THE INVENTION

Synthesis

The compounds of Formula I can be prepared by one or more of the methods described below in Equations 1–4.

As shown in Equation 1, compounds of Formula I where Q is $N(R_2)C(O)NHA$ (Ia) can be prepared by reacting the sulfonamides of Formula II with two equimolar amounts or more of an appropriate methyl carbamate of Formula III in the presence of two or more equivalents of trimethylaluminum.

Equation 1

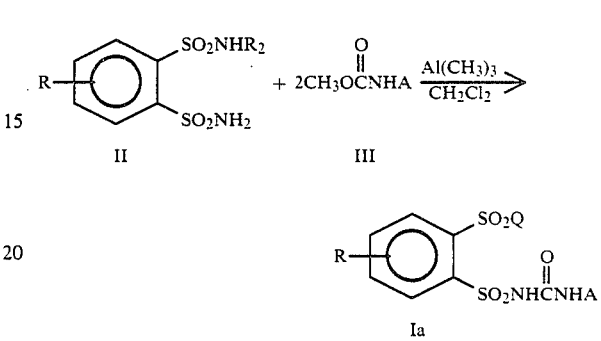

The reaction is carried out at 25°–80° C. in a solvent such as methylene chloride or 1,2-dichloroethane for 10 to 96 hours under an inert atmosphere as taught in EPO Publication No. 79,683 (published May 25, 1983).

The required carbamates III are prepared by reacting the corresponding amines IV with dimethylcarbonate or methyl chloroformate in the presense of a strong base.

Alternatively, compounds of Formula Ia can be prepared by reacting a sulfonylcarbamate of Formula V with 2 or more equivalents of an appropriate amine of Formula IV, as shown in Equation 2.

Equation 2

$$\underset{V}{R{-}\underset{SO_2NHCO_2C_6H_5}{\overset{\overset{R_2}{|}}{\underset{}{SO_2NCO_2C_6H_5}}}} + 2H_2NA \underset{Dioxane}{\overset{\triangle}{\longrightarrow}} Ia$$
$$\phantom{xxxxxxxxxxxxxxxxxxxx} IV$$

The reaction is carried out at 50° to 100° C. in a solvent such as dioxane for 0.5 to 24 hours, as taught in EPO publication No. 44807. The required carbamates are prepared by reacting the corresponding sulfonamide II with two or more equivalents of diphenylcarbonate in the presence of a strong base.

Compounds of Formula I, where Q is other than $$\overset{R_2}{\underset{|}{-N-C(O)NHA}} \text{ (Ib)},$$

can be prepared by reacting the sulfonamides of Formula VI with an appropriate methylcarbamate of Formula III in the presence of an equimolar amount of trimethylaluminum as shown in Equation 3.

Equation 3

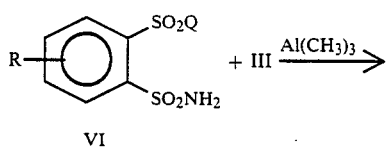

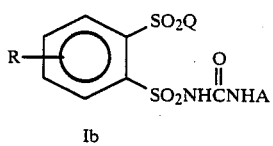

The reaction is carried out at 25° to 80° C. in a solvent such as methylene chloride or 1,2-dichloroethane for 10 to 96 hours under an inert atmosphere as taught in EPO Publication No. 79, 683.

Alternatively, compounds of Formula Ib can be prepared by reacting a sulfonylcarbamate of Formula III with an appropriate amine of Formula IV as shown in Equation 4.

Equation 4

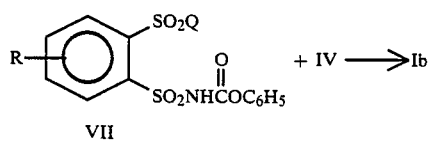

The reaction is carried out at 50° to 100° C. in a solvent such as dioxane for 0.5 to 24 hours as taught in EPO publication No. 44807. The required carbamates VII are prepared by reacting the corresponding sulfonamide VI with diphenylcarbonate in the presence of a strong base.

The compounds of Formula Ib can also be prepared by reacting a sulfonamide of Formula VI with phenylcarbamates of Formula IIIa in the presence of base as shown in Equation 5.

Equation 5

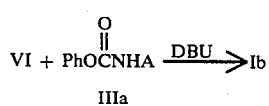

The reaction is carried out at 0° to 50° C. in an inert solvent such as acetonitrile for 0.1 to 24 hours in the presence of a base such as 1,8-diazabicyclo-[5.4.0]-undec-7-ene (DBU) as taught in EPO Publication No. 44,807. The required carbamate IIIa is prepared by reacting amine III with diphenylcarbonate or phenylchloroformate in the presence of base.

The intermediate sulfonamides of Formula II, where $R_2$ is H (IIa), can be prepared by reacting a 1,2-benzenedisulfonylazide of Formula VIII with a reducing agent such as sodium borohydride as shown in Equation 6.

Equation 6

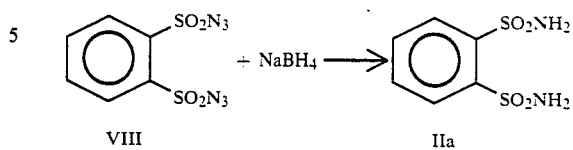

The reaction is carried out at −20° to 70° C. in a solvent such as ethanol for 10 to 96 hours.

The required 1,2-benzenedisulfonylazide VIII can be prepared by reacting a o-flurosulfonylbenzenesulfonyl chloride of Formula X with sodium azide as shown in Equation 7.

Equation 7

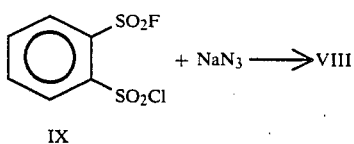

The reaction is carried out at 0° to 60° C. in a solvent such as water or methanol for 10 to 96 hours.

Alternatively, compounds of Formula VIII can be prepared by reacting a 1,2-benzenedisulfonyl chloride of Formula X with sodium azide as shown in Equation 8.

Equation 8

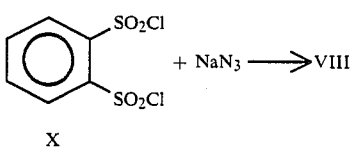

The reaction is carried out at 0° C. to 50° C. in a solvent such as methanol or water for 0.2 to 96 hours according to the teaching of R. A. Abramovitch and G. N. Knaus, *J. Org. Chem.*, 40, 883 (1975).

The intermediate sulfonamides of Formula II where $R_2$ is $CH_3$ (IIb) can be prepared by reacting a 2-(methylamino)sulfonylbenzenesulfonylazide of Formula XI with a reducing agent such as sodium borohydride as shown in Equation 9.

Equation 9

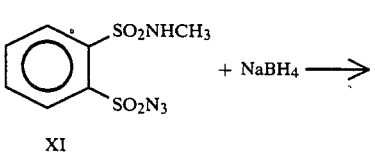

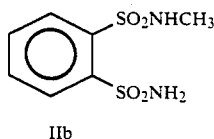

The reaction is carried out at −20° C. to 60° C. in a protic solvent such as ethanol for 10 to 96 hours under an inert atmosphere.

The required 2-(methylamino)sulfonylbenzenesulfonylazide XI can be prepared by reacting a N-methyl-o-fluorosulfonylbenzenesulfonamide of Formula XII with sodium azide as shown in Equation 10.

Equation 10

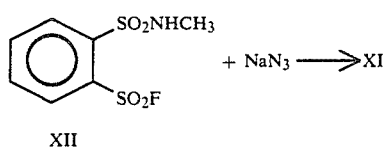

The reaction is carried out at −20° to 80° C. in a protic solvent such as water or methanol for 0.5 to 90 hours.

The required N-methyl-o-fluorosulfonylbenzenesulfonamide XII can be prepared by reacting a o-fluorosulfonylbenzenesulfonyl chloride IX with two equivalents of methylamine as shown in Equation 11.

Equation 11

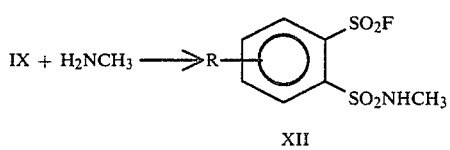

The reaction is carried out at −20° to 60° C. in an inert protic solvent such as tetrahydrofuran for 0.5 to 96 hours.

The intermediate sulfonamides of Formula VI where Q is

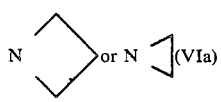 (VIa)

can be prepared by reacting a sulfonyl fluoride of Formula XIII with ammonia as shown in Equation 12.

Equation 12

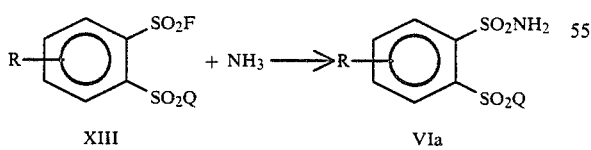

The reaction is carried out at 20°–80° C. in an inert protic solvent such as tetrahydrofuran for 2–90 hours. The required sulfonyl fluoride (XIII) is prepared by reacting a o-fluorosulfonylbenzenesulfonyl chloride of Formula IX with azetidine or aziridine in the presence of a base such as triethylamine as shown in Equation 13 where Q is either

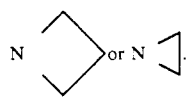

Equation 13

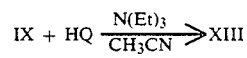

The reaction is carried out at −20° to 60° C. in an inert solvent such as acetonitrile for 2–90 hours.

The intermediate sulfonamides of Formula VI, where Q is $N(R_2)C(O)N(R_4)R_5$ with $R_4$ and $R_5$ being other than H, can be prepared by reacting the sulfonamides of Formula IIa with a carbamyl chloride of Formula XIV in the presence of a base such as triethylamine as shown in Equation 14.

Equation 14

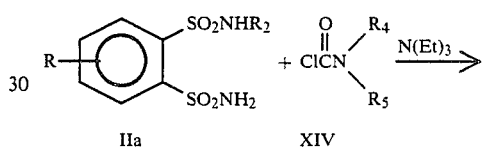

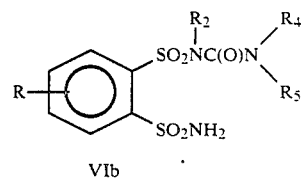

The reaction is carried out at 25°–110° C. in a solvent such as diglyme for 10 to 296 hours.

Alternatively, the intermediate sulfonamides of Formula VIb can be prepared by reacting the sulfonamides of Formula II with a carbamate of Formula XV in the presence of trimethylaluminum as shown in Equation 15.

Equation 15

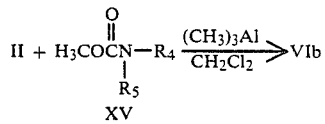

The reaction is carried out at 25° to 80° C. in a solvent such as methylene chloride or 1,2-dichloroethane for 10 to 96 hours under an inert atmosphere.

The intermediate sulfonamides of Formula VI where Q is $-N(R_2)C(O)R_3$ (VIc) can be prepared by reacting the sulfonamides of Formula II with an acid chloride of Formula XVI in the presence of a base such as triethylamine as shown in Equation 16.

Equation 16

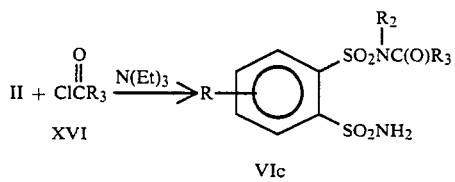

The reaction is carried out 25°–110° C. in a solvent such as diglyme for 10 to 296 hours.

Alternatively, the intermediate sulfonamides of Formula VIc can be prepared by reacting the sulfonamides of Formula II with a methyl ester of Formula XVII in the presence of trimethylaluminum as shown in Equation 17.

Equation 17

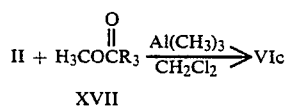

The reaction is carried out at 25° to 80° C. in a solvent such as methylene chloride or 1,2-dichloroethane for 10 to 96 hours under an inert atmosphere.

The intermediate sulfonamides of Formula VI where Q is $N(R_2)CO_2R_6$ (VId) can be prepared by reacting the sulfonamides of Formula II with a chloroformate of Formula XVIII in the presence of a base such as triethylamine as shown in Equation 18.

Equation 18

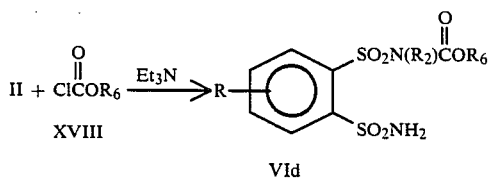

The reaction is carried out at 25°–110° C. in a solvent such as diglyme for 10 to 296 hours under an inert atmosphere.

The intermediate sulfonamides of Formula VI where Q is $N(R_2)C(O)NHR_4$ (VIe) can be prepared by reacting the sulfonamide of Formula II with the isocyanate of Formula XIX in the presence of a base such as 4-N,N-dimethylpyridine as shown in Equation 19.

Equation 19

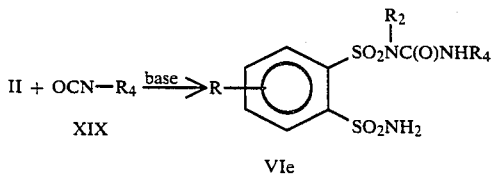

The reaction is carried out at 25°–110° C. in a solvent such as diglyme for 10 to 296 hours.

The intermediate sulfonamides VI where $Q_1$ is

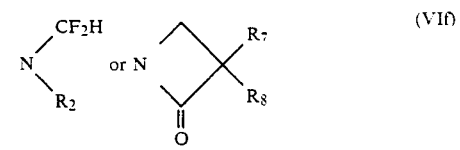

can be prepared by reacting a sulfonyl chloride of Formula XX with ammonia as shown in Equation 20.

Equation 20

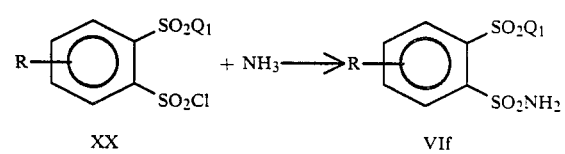

The reaction is carried out at 20°–80° C. in an inert aprotic solvent such as tetrahydrofuran for 2-90 hours. The required sulfonyl chloride XX can be prepared from the corresponding chlorides of Formula XXI by the two step sequence as shown in Equation 21.

Equation 21

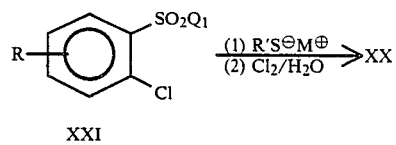

The first step involves nucleophilic displacement of the chlorine atom with an alkyl or benzyl mercaptide to give an intermediate sulfide. The reaction can be carried out at 25° to 80° C. in a polar solvent such as DMF for 0.5 to 24 hours. The sulfide is then oxidatively chlorinated to the desired sulfonyl chloride by the addition of molecular chlorine or a chlorine equivalent to the sulfide in the presence of water at 15° to 80° C. in an aliphatic carboxylic acid solvent such as acetic acid or an inert organic solvent such as dichloroethane for 1 to 24 hours. The required chlorides of Formula XXIa can be prepared by reacting a o-chlorosulfonyl isocyanate of Formula XXIIa with an alkene of Formula XXIII as shown in Equation 22.

Equation 22

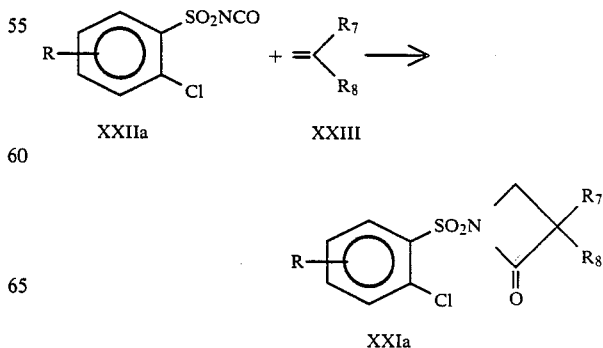

The reaction is carried out at 25°–120° C. in a solvent such as nitromethane for 2–90 hours under an inert atmosphere.

The required chlorides of Formula XXIb can be prepared by reacting a o-chlorobenzenesulfonamide of Formula XXIIb with ClCF$_2$H in the presence of a base such as sodium hydroxide, potassium hydroxide or potassium carbonate as shown in Equation 23.

Equation 23

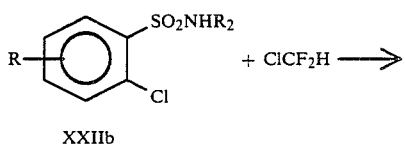

XXIIb

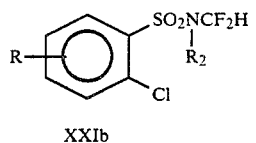

XXIb

The reaction is carried out at 25°–170° C. in a solvent such as DMF or dioxane for 2–90 hours under an inert atmosphere.

The amines of Formula IV in Equations 2 and 4 are also important intermediates for the preparation of the compounds of this invention and are described below.

The pyrimidines and triazines of Formula (IVa) to (IVd) below are either known or can be prepared by obvious methods by one skilled in the art.

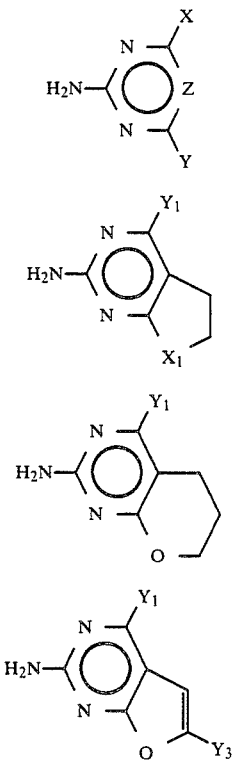

For a review of the synthesis and reactions of 2-aminopyrimidines (IVa, Z=CH) see *The Chemistry of Heterocyclic Compounds*, Vol. 16, John Wiley and Sons, New York (1962). For a review of the synthesis and reactions of 2-amino-s-triazine (IVa, Z=N) see *The Chemistry of Heterocyclic Compounds*, Vol. 13, John Wiley, New York (1959), F. C. Schaefer, U.S. Pat. No. 3,154,547 and F. C. Schaefer and K. R. Huffman, *J. Org. Chem.*, 28, 1812 (1963). The synthesis of the bicyclic amines IVb and IVc is taught in U.S. Pat. No. 4,339,267. The synthesis of bicyclic amines IVd is taught in European patent application (EP-A) No. 46,677 (published Mar. 3, 1982).

The amines of Formula IVa where X is OCF$_2$H, OCH$_2$F or CF$_3$ and/or Y is OCF$_2$H can be prepared by methods taught in South African patent application No. 825,045, or by suitable modifications that would be obvious to one skilled in the art.

The pyrimidines of Formula IVa (Z=CH) where Y is —CH(OCH$_2$)$_2$, —CH(OCH$_2$CH$_3$)$_2$,

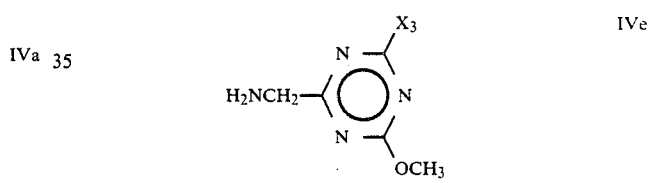

can be prepared according to the methods taught in European patent application (EP-A) No. 84,224, published July 27, 1983 or suitable modifications thereof known to one skilled in the art.

The triazine amines of Formula IVe where X$_3$ is CH$_3$ or OCH$_3$ can be prepared according to the teachings of European patent application (EP-A) No. 94,260, published Nov. 16, 1983.

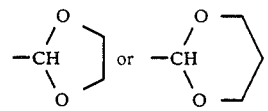

The preparation of 3-amino-1,2,4-triazoles of Formula IVf is taught in European patent application (EP-A) No. 73,562, published Mar. 9, 1983.

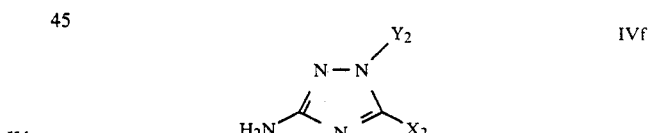

EXAMPLE 1

N-[(4,6-dimethoxypyrimidin-2-yl)aminocarbonyl]-1,2-benzenesulfonamide

To a suspension of 0.7 g of 1,2-benzenedisulfonamide and 1.5 ml of trimethylaluminum in 70 ml of anhydrous methylene chloride was added 0.6 g of 4,6-dimethoxypyrimidin-2-ylcarbamic acid methyl ester under N$_2$ with stirring. After addition, the mixture was stirred at room temperature for 30 minutes and was then heated to reflux for 12 hours. The reaction mixture was then cooled down to room temperature. To this mixture was added 50 ml of methylene chloride, 100 ml of water, 10 ml of acetic acid and 5 drops of concentrated hydrochloric acid. The mixture was then stirred at room temperature for 20 minutes and was filtered. The organic layer was then separated, washed with water, dried over sodium sulfate and concentrated. The residue was then chromatographed on silica gel ($CH_2Cl_2$/acetic acid 1:1) to yield 0.2 g of N-[(4,6-dimethoxypyrimidin-2-yl)aminocarbonyl]-1,2-benzenedisulfonamide, m.p. 192°-193° C.

NMR(DMSO-$d_6$)δ: 3.92 (6H, s); 5.83 (1H, s); 7.35 (2H, s); 7.8-8.6 (4H, m); 10.5 (1H, s); 12.8 (1H, bs).

EXAMPLE 2

N,N'-Bis[(4,6-dimethoxypyrimidin-2-yl)aminocarbonyl]-1,2-benzenedisulfonamide

To a suspension of 0.5 g of 1,2-benzenedisulfonamide and 2.5 ml of trimethylaluminum in 50 ml of anhydrous methylene chloride was added 1 g of 4,6-dimethoxypyrimidin-2-ylcarbamic acid methyl ester under $N_2$ with stirring. After addition, the mixture was stirred at room temperature for 30 minutes and was then heated to reflux for 12 hours. The reaction mixture was then cooled down to room temperature. To this mixture was added 50 ml of methylene chloride, 100 ml of water, 10 ml of acetic acid and 5 drops of concentrated hydrochloric acid. The mixture was then stirred at room temperature for 20 minutes and filtered. The organic layer was separated, washed with water, dried over $MgSO_4$ and concentrated. The residue was stirred in n-butyl chloride for 2 hours and filtered. The solid was washed with copious amount of ethyl acetate and then dried to yield 0.18 g of N,N'-bis[(4,6-dimethoxypyrimidin-2-yl)aminocarbonyl]-1,2-benzenedisulfonamide, m.p. 201°-203° C.

NMR(DMSO-$d_6$)δ: 3.92 (12H, s); 5.95 (2H, s); 7.8-8.6 (4H); 10.2 (2H, s); 12.2 (2H, bs).

EXAMPLE 3

1,2-Benzenedisulfonamide (IIa)

One gram of 1,2-benzenedisulfulnylazide was added portionwise to 0.4 gm sodium borohydride in 15 ml of ethyl alcohol with stirring and cooling. After addition, the mixture was stirred with cooling (ice/acetone bath) for 2 hours and filtered. The solid was washed with cold ethyl alcohol and ether to yield 0.8 g of 1,2-benzenedisulfonamide, m.p. 250° C. Mass spec. (M/e) 236

EXAMPLE 4

2-(Azetidin-1-ylsulfonyl)-N-[(4,6-dimethoxy-1,3,5-triazin-2-yl)aminocarbonyl]benzenesulfonamide In a dry flask under nitrogen was placed 1.20 gram of 2-(azetidin-1-ylsulfonyl)benzenesulfonamide, 50 ml of dry dichloromethane and 2.48 ml of 2M trimethylaluminum in toluene. To this was added 0.885 g of 4,6-dimethoxy-1,3,5-triazin-2-ylcarbamic acid methyl ester and the resultant solution was heated to reflux for 12 hours. The solution was washed with 50 ml of a water/acetic acid/1N HCl solution (40:10:0.4). The organic fraction was concentrated and chromatographed on silica gel (ethyl acetate/methylene chloride (15:85)). The slower moving portions were collected, treated with ethyl acetate and dried to give 0.45 g of a solid, m.p. 175°-177° C.

HNMR ($CDCl_3$/$CF_3CO_2H$, 90 MHz)δ: 2.0-2.35 (m, 3H); 4.05 (t, 4H, J 8 Hz); 4.15 (s, 6H); 7.7-8.7 (m, 4H); IR (nujol) 1700 $cm^{-1}$.

EXAMPLE 5

2-(Azetidin-1-ylsulfonyl)benzenesulfonamide

In a 1-1 flask was placed 9.8 g of 2-(azetidin-1-ylsulfonyl)benzenesulfonyl fluoride and 500 ml of THF. Then 9 ml of ammonia was added and the mixture was refluxed for two days. Four 25 ml portions of liquid ammonia were then added to the refluxing solution over a 48 hour period. The reaction mixture was concentrated and the residue chromatographed on silica gel (dichloroethane). The desired product was collected to give 4.9 g of a solid m.p. 121°-123° C.

NMR($CDCl_3$/DMSO-$d_6$, 90 mmHz)δ: 1.9-2.30 (m, 2H); 3.95 (t, 4H); 6.90 (bs, 2H); 7.65-8.35 (m, 4H).

IR(nujol) $cm^{-1}$ 3420 and 3300 ($NH_2$), 1340 and 1170 ($SO_2$).

EXAMPLE 6

2-(1-Azetidinylsulfonyl)benzenesulfonyl fluoride

In a flask was placed 9.24 g of 2-fluorosulfonylbenzenesulfonyl chloride and 200 ml of dry acetonitrile. The resultant solution was cooled to 0° C. An addition funnel was charged with 2 g of azetidine, 4.95 ml of triethylamine and 50 ml of acetonitrile. This solution was added dropwise to the first solution. After stirring overnight the solvent was evaporated under reduced pressure. The residue was partitioned between dichloromethane and 1N hydrochloric acid. The organic layer was separated, dried and concentrated to give 9.80 g of a solid, m.p. 93° C.

NMR ($CDCl_3$, 90 MHz)δ: 2.20 (m, 2H); 4.10 (t, 4H); 7.6-8.50 (m, 4H).

IR (nujol) $cm^{-1}$ 1360(b); 1165(b)($SO_2$).

EXAMPLE 7

N-Difluoromethyl-N-methyl-2-chlorobenzenesulfonamide

A mixture of 260 ml of dioxane, 260 ml of 50% sodium hydroxide aqueous solution and 55 g (0.2683 mole) of N-methyl-2-chlorobenzenesulfonamide was heated to 70°-75° C. To this mixture was then added 37.6 ml of Freon 22 ® ($CF_2HCl$) dropwise over a period of 1 hour. The solution was heated at 70°-75° C. for an additional 12 hours and was then allowed to cool to room temperature while stirring. The reaction mixture was then extracted with one portion of ether and one portion of ethyl acetate. The combined organic layers were washed with water, 1N HCl solution and brine. The organic layer was then concentrated and the residue was chromatographed on silica gel (ethyl acetate/Hexane 1:1) to yield 29.95 g of N-difluoromethyl-N-methyl-2-chlorobenzenesulfonamide as an oil.

NMR ($CDCl_3$)δ: 2.86(3H.s); 7.08(1H, t); 7.4-8.2 (4H, m).

EXAMPLE 8

N-Difluoromethyl-N-methyl-2-(n-propylthio)benzenesulfonamide

To a mixture of 14.62 ml of n-propylmercaptan, 16.3 g of potassium t-butoxide and 400 ml of DMF at 0° C. was added 27.45 g (0.1076 mole) of N-difluoromethyl-N-methyl-2-chlorobenzenesulfonamide in 100 ml of DMF. The reaction mixture was stirred at room temperature for 2 days and then at 60° C. for 4 hours. The mixture was then concentrated and the residue was partitioned between 1N HCl solution and methylene chloride. The organic layer was separated, dried over $MgSO_4$, and concentrated. The residue was chromatographed on silica gel (Hexane/chloroform 3:2) to yield 24.63 g of N-difluoromethyl-N-methyl-2-(n-propylthio)benzenesulfonamide as an oil.

NMR (CDCl₃)δ: 1.05(3H, t); 1.50–1.80 (2H, m); 2.81(3H, s); 2.98(2H, t); 7.18 (1H, t); 7.2–8.05 (4H, m).

EXAMPLE 9

N-Difluoromethyl-N-methyl-1,2-benzenedisulfonamide

To a mixture of 23.08 g (0.078 mole) of N-difluoromethyl-N-methyl-2-(n-propylthio)benzenesulfonamide, 160 ml of acetic acid and 3.0 ml of distilled water at 0° C. was added 16.59 ml of chlorine dropwise over 15 minutes. The reaction mixture was allowed to warm to ambient temperature and was stirred at ambient temperature for 2 hours. The reaction mixture was then poured into ice water with a solid precipitating. The solid was washed with water and small amount of pentane to give 20.6 g of material (m.p. 89°–91° C.) after being air dried. The filtrate was extracted with 500 ml of CH₂Cl₂. The CH₂Cl₂ layer was separated, washed with brine, dried over MgSO₄, and concentrated to give 10.16 g of a light yellow oil. The solid and the oil were then combined and dissolved in 300 ml of anhydrous THF. To this solution was added 50 ml of ammonium hydroxide dropwise. The reaction mixture was heated to reflux. After refluxing for 4 hours, an additional 30 ml of ammonium hydroxide was added. The reaction was refluxed for another 12 hours. To this mixture was then added another 50 ml of ammonium hydroxide. The solution was then refluxed for another 12 hours. To the reaction mixture was then added 50 ml of ethyl acetate. The resulting solution was washed with water, dried over MgSO₄ and concentrated. The residue was then triturated with CH₂Cl₂/acetone (1:1) with a solid precipitating. The solid was then collected by filtration to yield 3.93 g of N-difluoromethyl-N-methyl-1,2-benzenedisulfonamide, m.p. 128° C. The filtrate was concentrated and the residue was chromatographed on silica gel to yield another 8.5 g of the title compound.

NMR (DMSO-d₆)δ: 2.85 (3H, bs); 7.26 (1H, t); 7.5(2H, bs); 7.75–8.30 (4H, m).

TABLE I

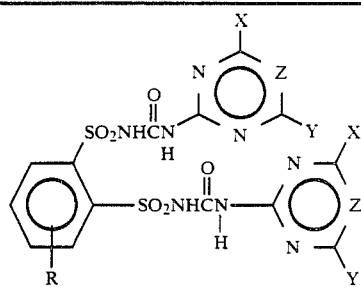

| R | X | Y | Z | m.p. (°C.) |
|---|---|---|---|---|
| H | CH₃ | CH₃ | CH | 186–189° C. (d) |
| H | OCH₃ | CH₃ | CH | 145–146° C. (d) |
| H | OCH₃ | OCH₃ | CH | 201–203° C. (d) |
| H | CH₃ | C₂H₅ | CH | |
| H | OCH₃ | C₂H₅ | CH | |
| H | CH₃ | OC₂H₅ | CH | |
| H | OCH₃ | OC₂H₅ | CH | |
| H | CH₃ | CH₂OCH₃ | CH | |
| H | OCH₃ | CH₂OCH₃ | CH | |
| H | Br | OC₂H₅ | CH | |
| H | Br | OCH₃ | CH | |
| H | OCH₃ | N(CH₃)₂ | CH | |
| H | CH₃ | CH₃ | N | 123–125° C. (d) |
| H | OCH₃ | CH₃ | N | 111–112° C. (d) |
| H | OCH₃ | OCH₃ | N | 152–153° C. (d) |
| H | CH₃ | C₂H₅ | N | |
| H | OCH₃ | C₂H₅ | N | |
| H | CH₃ | OC₂H₅ | N | |

TABLE I-continued

| R | X | Y | Z | m.p. (°C.) |
|---|---|---|---|---|
| H | OCH₃ | OC₂H₅ | N | |
| H | CH₃ | CH₂OCH₃ | N | |
| H | OCH₃ | CH₂OCH₃ | N | |
| H | OCF₂H | OCH₃ | N | |
| H | OCH₂CH₃ | OCH₃ | N | |
| H | CH₃ | NHCH₃ | CH | |
| H | OCH₃ | NHCH₃ | CH | |
| H | CH₃ | NHCH₃ | N | |
| H | OCH₃ | NHCH₃ | N | |
| H | OCH₃ | N(CH₃)₂ | N | |
| H | CH₃ | CH(OCH₃)₂ | CH | |
| H | OCH₃ | CH(OCH₃)₂ | CH | |
| H | CH₃ | O–CH(–O–) (dioxolane) | CH | |
| H | OCH₃ | O–CH(–O–) (dioxolane) | CH | |
| H | CH₃ | CH(OCH₃)₂ | N | |
| H | OCH₃ | CH(OCH₃)₂ | N | |
| H | CH₃ | O–CH(–O–) (dioxolane) | N | |
| H | OCH₃ | O–CH(–O–) (dioxolane) | N | |
| H | Cl | OCH₃ | CH | |
| H | Cl | OC₂H₅ | CH | |
| H | Cl | NHCH₃ | CH | |
| H | Cl | N(CH₃)₂ | CH | |
| H | CH₃ | SCH₃ | N | |
| H | OCH₃ | SCH₃ | N | |
| H | CH₃ | SCH₃ | CH | |
| H | OCH₃ | SCH₃ | CH | |
| 6-Cl | OCH₃ | OCH₃ | CH | |
| 6-Cl | OCH₃ | N(CH₃)₂ | CH | |
| 5-Cl | CH₃ | OCH₃ | CH | |
| 5-Cl | CH₃ | CH₃ | CH | |
| 4-Cl | CH₃ | N(CH₃)₂ | CH | |
| 4-Cl | CH₃ | CH₃ | N | |
| 3-Cl | OCH₃ | CH₃ | N | |
| 3-Cl | OCH₃ | OCH₃ | N | |
| 6-Br | CH₃ | C₂H₅ | N | |
| 6-Br | OCH₃ | C₂H₅ | N | |
| 5-Br | CH₃ | OC₂H₅ | N | |
| 5-Br | OCH₃ | OC₂H₅ | N | |
| 4-Br | CH₃ | CH₂OCH₃ | N | |
| 3-Br | OCH₃ | CH₂OCH₃ | N | |
| 6-F | OCH₃ | OCH₃ | N | |
| 5-F | OCH₃ | CH₃ | N | |
| 4-F | OCH₃ | N(CH₃)₂ | N | |

TABLE I-continued

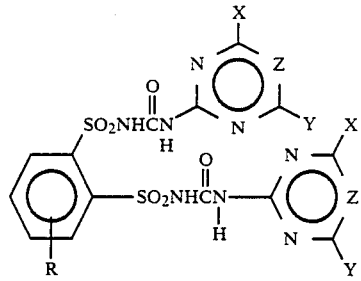

| R | X | Y | Z | m.p. (°C.) |
|---|---|---|---|---|
| 3-F | CH₃ | O-CH-O (dioxolane) | CH | |
| 6-OCH₃ | OCH₃ | O-CH-O (dioxolane) | CH | |
| 5-OCH₃ | CH₃ | O-CH-O (dioxolane) | N | |
| 5-OCH₃ | OCH₃ | O-CH-O (dioxolane) | N | |
| 4-OCH₃ | Cl | OCH₃ | CH | |
| 3-OCH₃ | CH₃ | CH₃ | CH | |
| 6-CF₃ | OCH₃ | CH₃ | CH | |
| 5-CF₃ | OCH₃ | OCH₃ | CH | |
| 4-CF₃ | CH₃ | C₂H₅ | CH | |
| 4-CF₃ | OCH₃ | C₂H₅ | CH | |
| 3-CF₃ | CH₃ | OC₂H₅ | CH | |
| H | OCH₃ | CH₂F | CH | |
| H | CH₃ | CH₂F | CH | |
| H | OCH₃ | CH₂F | N | |
| H | CH₃ | CH₂F | N | |

TABLE IIa

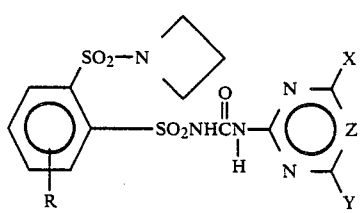

| R | X | Y | Z | m.p. (°C.) |
|---|---|---|---|---|
| H | CH₃ | CH₃ | CH | 200–205° C. |
| H | OCH₃ | CH₃ | CH | 220–221° C. |
| H | OCH₃ | OCH₃ | CH | 218–220° C. |
| H | CH₃ | C₂H₅ | CH | |
| H | OCH₃ | C₂H₅ | CH | |
| H | CH₃ | OC₂H₅ | CH | |
| H | OCH₃ | OC₂H₅ | CH | |
| H | CH₃ | CH₂OCH₃ | CH | |
| H | OCH₃ | CH₂OCH₃ | CH | |
| H | Br | OC₂H₅ | CH | |
| H | Br | OCH₃ | CH | |
| H | OCH₃ | N(CH₃)₂ | CH | |
| H | CH₃ | CH₃ | N | 211° C. |

TABLE IIa-continued

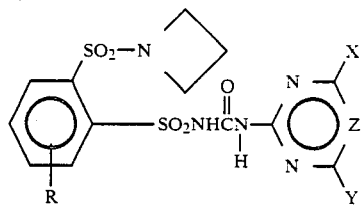

| R | X | Y | Z | m.p. (°C.) |
|---|---|---|---|---|
| H | OCH₃ | CH₃ | N | 201° C. |
| H | OCH₃ | OCH₃ | N | 175–177° C. |
| H | CH₃ | C₂H₅ | N | |
| H | OCH₃ | C₂H₅ | N | |
| H | CH₃ | OC₂H₅ | N | |
| H | OCH₃ | OC₂H₅ | N | |
| H | CH₃ | CH₂OCH₃ | N | |
| H | OCH₃ | CH₂OCH₃ | N | |
| H | OCF₂H | OCH₃ | N | |
| H | OCH₂CH₃ | OCH₃ | N | |
| H | OCH₃ | N(CH₃)₂ | N | |
| H | CH₃ | CH(OCH₃)₂ | CH | |
| H | OCH₃ | CH(OCH₃)₂ | CH | |
| H | CH₃ | O-CH-O (dioxolane) | CH | |
| H | OCH₃ | O-CH-O (dioxolane) | CH | |
| H | CH₃ | CH(OCH₃)₂ | N | |
| H | OCH₃ | CH(OCH₃)₂ | N | |
| H | CH₃ | O-CH-O (dioxolane) | N | |
| H | OCH₃ | O-CH-O (dioxolane) | N | |
| H | Cl | OCH₃ | CH | |
| H | Cl | NHCH₃ | CH | |
| H | Cl | OC₂H₅ | CH | |
| H | Cl | N(CH₃)₂ | CH | |
| H | CH₃ | SCH₃ | N | |
| H | OCH₃ | SCH₃ | N | |
| H | CH₃ | SCH₃ | CH | |
| H | OCH₃ | SCH₃ | CH | |
| 6-Cl | OCH₃ | OCH₃ | CH | |
| 6-Cl | OCH₃ | N(CH₃)₂ | CH | |
| 5-Cl | CH₃ | OCH₃ | CH | |
| 5-Cl | CH₃ | CH₃ | CH | |
| 4-Cl | CH₃ | N(CH₃)₂ | CH | |
| 4-Cl | CH₃ | CH₃ | N | |
| 3-Cl | OCH₃ | CH₃ | N | |
| 3-Cl | OCH₃ | OCH₃ | N | |
| 6-Br | CH₃ | C₂H₅ | N | |
| 6-Br | OCH₃ | C₂H₅ | N | |
| 5-Br | CH₃ | OC₂H₅ | N | |
| 5-Br | OCH₃ | OC₂H₅ | N | |
| 4-Br | CH₃ | CH₂OCH₃ | N | |
| 3-Br | OCH₃ | CH₂OCH₃ | N | |
| 6-F | OCH₃ | OCH₃ | N | |
| 5-F | OCH₃ | CH₃ | N | |
| 4-F | OCH₃ | N(CH₃)₂ | N | |

TABLE IIa-continued

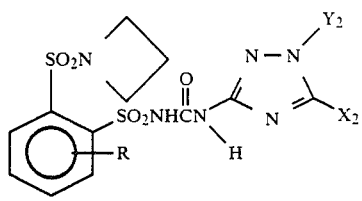

| R | X | Y | Z | m.p. (°C.) |
|---|---|---|---|---|
| 3-F | CH₃ | O-CH-O (dioxolane) | CH | |
| 6-OCH₃ | OCH₃ | O-CH-O (dioxolane) | CH | |
| 5-OCH₃ | CH₃ | O-CH-O (dioxolane) | N | |
| 5-OCH₃ | OCH₃ | O-CH-O (dioxolane) | N | |
| 4-OCH₃ | Cl | OCH₃ | CH | |
| 3-OCH₃ | CH₃ | CH₃ | CH | |
| 6-CF₃ | OCH₃ | CH₃ | CH | |
| 5-CF₃ | OCH₃ | OCH₃ | CH | |
| 4-CF₃ | CH₃ | C₂H₅ | CH | |
| 4-CF₃ | OCH₃ | C₂H₅ | CH | |
| 3-CF₃ | CH₃ | OC₂H₅ | CH | |
| H | CH₃ | CH₂F | CH | |
| H | OCH₃ | CH₂F | CH | |
| H | CH₃ | CH₂F | N | |
| H | OCH₃ | CH₂F | N | |
| H | CH₃ | NHCH₃ | CH | |
| H | OCH₃ | NHCH₃ | CH | |
| H | CH₃ | NHCH₃ | N | |
| H | OCH₃ | NHCH₃ | N | |

TABLE IIb

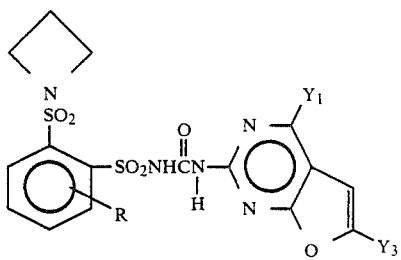

| R | X₁ | Y₁ | m.p. (°C.) |
|---|---|---|---|
| H | O | CH₃ | |
| H | O | OCH₃ | |
| H | CH₂ | CH₃ | |
| H | CH₂ | OCH₃ | |
| H | O | Cl | |
| 5-Cl | O | CH₃ | |
| 3-Cl | CH₂ | OCH₃ | |
| 5-CF₃ | CH₂ | CH₃ | |
| 4-CF₃ | O | CH₃ | |
| 6-Br | CH₂ | OCH₃ | |
| 4-F | O | H | |
| H | O | H | |

TABLE IIb-continued

| R | X₁ | Y₁ | m.p. (°C.) |
|---|---|---|---|
| 5-OCH₃ | O | OCH₃ | |

TABLE IIc

| R | Y₂ | X₂ |
|---|---|---|
| H | CH₃ | SCH₃ |
| H | CH₂CF₃ | SCH₃ |
| H | CH₃ | OCH₃ |
| H | C₂H₅ | SCH₃ |
| H | C₂H₅ | CH₃ |
| H | C₂H₅ | OCH₃ |
| H | CH₃ | CH₃ |
| H | CH₂CF₃ | OCH₃ |
| 6-Cl | CH₃ | OCH₃ |
| 5-Cl | CH₃ | OCH₃ |
| 4-Cl | CH₃ | OCH₃ |
| 5-Br | CH₃ | OCH₃ |
| 4-Br | CH₃ | OCH₃ |
| 4-F | CH₃ | OCH₃ |
| 3-F | CH₃ | OCH₃ |
| 6-OCH₃ | CH₃ | OCH₃ |
| 5-OCH₃ | CH₃ | OCH₃ |
| 4-OCH₃ | CH₃ | OCH₃ |
| 6-CF₃ | CH₃ | OCH₃ |
| 5-CF₃ | CH₃ | OCH₃ |

TABLE IId

| R | Y₁ | Y₃ | m.p. (°C.) |
|---|---|---|---|
| H | CH₃ | H | |
| H | OCH₃ | CH₃ | |
| H | Cl | CH₃ | |
| 5-Cl | OCH₃ | H | |
| 4-Cl | CH₃ | CH₃ | |
| 5-Br | OCH₃ | CH₃ | |
| 4-Br | CH₃ | CH₃ | |
| 4-F | OCH₃ | H | |
| 3-F | CH₃ | CH₃ | |
| H | H | CH₃ | |
| 5-OCH₃ | CH₃ | CH₃ | |
| 4-OCH₃ | OCH₃ | CH₃ | |
| 6-CF₃ | CH₃ | CH₃ | |

TABLE IId-continued

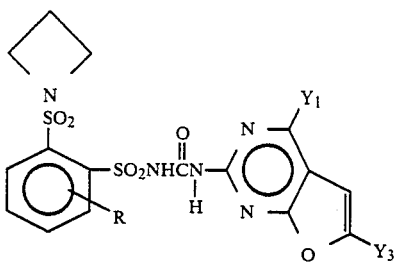

| R | Y₁ | Y₃ | m.p. (°C.) |
|---|----|----|-----------|
| 5-CF₃ | OCH₃ | CH₃ | |

TABLE IIe

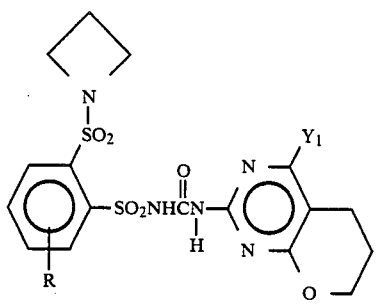

| R | Y₁ | m.p. (°C.) |
|---|----|-----------|
| H | CH₃ | |
| H | Cl | |
| H | OCH₃ | |
| H | H | |
| 6-Cl | CH₃ | |
| 5-Br | OCH₃ | |
| 4-Cl | OCH₃ | |
| 3-F | OCH₃ | |
| 5-OCH₃ | OCH₃ | |
| 4-CH₃ | OCH₃ | |

TABLE IIf

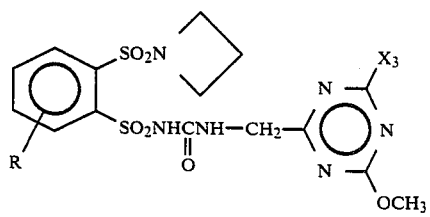

| R | X₃ | m.p. (°C.) |
|---|----|-----------|
| H | CH₃ | |
| H | OCH₃ | |
| 6-Cl | CH₃ | |
| 5-Br | OCH₃ | |
| 4-F | CH₃ | |
| 3-CF₃ | OCH₃ | |
| 5-CH₃ | CH₃ | |
| 4-OCH₃ | OCH₃ | |

TABLE IIIa

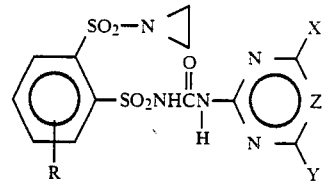

| R | X | Y | Z | m.p. (°C.) |
|---|---|---|---|-----------|
| H | CH₃ | CH₃ | CH | |
| H | OCH₃ | CH₃ | CH | |
| H | OCH₃ | OCH₃ | CH | |
| H | CH₃ | C₂H₅ | CH | |
| H | OCH₃ | C₂H₅ | CH | |
| H | CH₃ | OC₂H₅ | CH | |
| H | OCH₃ | OC₂H₅ | CH | |
| H | CH₃ | CH₂OCH₃ | CH | |
| H | OCH₃ | CH₂OCH₃ | CH | |
| H | Br | OC₂H₅ | CH | |
| H | Br | OCH₃ | CH | |
| H | OCH₃ | N(CH₃)₂ | CH | |
| H | CH₃ | CH₃ | N | |
| H | OCH₃ | CH₃ | N | |
| H | OCH₃ | OCH₃ | N | |
| H | CH₃ | C₂H₅ | N | |
| H | OCH₃ | C₂H₅ | N | |
| H | CH₃ | OC₂H₅ | N | |
| H | OCH₃ | OC₂H₅ | N | |
| H | CH₃ | CH₂OCH₃ | N | |
| H | OCH₃ | CH₂OCH₃ | N | |
| H | OCF₂H | OCH₃ | N | |
| H | OCH₂CH₃ | OCH₃ | N | |
| H | OCH₃ | N(CH₃)₂ | N | |
| H | CH₃ | CH(OCH₃)₂ | CH | |
| H | OCH₃ | CH(OCH₃)₂ | CH | |
| H | CH₃ | NHCH₃ | CH | |
| H | OCH₃ | NHCH₃ | CH | |
| H | CH₃ | NHCH₃ | N | |
| H | OCH₃ | NHCH₃ | N | |
| H | CH₃ | ⟨O-CH-O⟩ | CH | |
| H | OCH₃ | ⟨O-CH-O⟩ | CH | |
| H | CH₃ | CH(OCH₃)₂ | N | |
| H | OCH₃ | CH(OCH₃)₂ | N | |
| H | CH₃ | ⟨O-CH-O⟩ | N | |
| H | OCH₃ | ⟨O-CH-O⟩ | N | |
| H | Cl | OCH₃ | CH | |
| H | Cl | NHCH₃ | CH | |
| H | Cl | OC₂H₅ | CH | |
| H | Cl | N(CH₃)₂ | CH | |
| H | CH₃ | SCH₃ | N | |
| H | OCH₃ | SCH₃ | N | |
| H | CH₃ | SCH₃ | CH | |
| H | OCH₃ | SCH₃ | CH | |
| 6-Cl | OCH₃ | OCH₃ | CH | |
| 6-Cl | OCH₃ | N(CH₃)₂ | CH | |
| 5-Cl | CH₃ | OCH₃ | CH | |

TABLE IIIa-continued

[Structure: benzene ring with SO₂-N(aziridine) and SO₂NHC(O)NH-pyrimidine/triazine substituents, R on benzene, X, Y, Z on heterocycle]

| R | X | Y | Z | m.p. (°C.) |
|---|---|---|---|---|
| 5-Cl | CH₃ | CH₃ | CH | |
| 4-Cl | CH₃ | N(CH₃)₂ | CH | |
| 4-Cl | CH₃ | CH₃ | N | |
| 3-Cl | OCH₃ | CH₃ | N | |
| 3-Cl | OCH₃ | OCH₃ | N | |
| 6-Br | CH₃ | C₂H₅ | N | |
| 6-Br | OCH₃ | C₂H₅ | N | |
| 5-Br | CH₃ | OC₂H₅ | N | |
| 5-Br | OCH₃ | OC₂H₅ | N | |
| 4-Br | CH₃ | CH₂OCH₃ | N | |
| 3-Br | OCH₃ | CH₂OCH₃ | N | |
| 6-F | OCH₃ | OCH₃ | N | |
| 5-F | OCH₃ | CH₃ | N | |
| 4-F | OCH₃ | N(CH₃)₂ | N | |
| 3-F | CH₃ | —O-CH-O— (dioxolane) | CH | |
| 6-OCH₃ | OCH₃ | —O-CH-O— (dioxolane) | CH | |
| 5-OCH₃ | CH₃ | —O-CH-O— (dioxolane) | N | |
| 5-OCH₃ | OCH₃ | —O-CH-O— (dioxolane) | N | |
| 4-OCH₃ | Cl | OCH₃ | CH | |
| 3-OCH₃ | CH₃ | CH₃ | CH | |
| 6-CF₃ | OCH₃ | CH₃ | CH | |
| 5-CF₃ | OCH₃ | OCH₃ | CH | |
| 4-CF₃ | CH₃ | C₂H₅ | CH | |
| 4-CF₃ | OCH₃ | C₂H₅ | CH | |
| 3-CF₃ | CH₃ | OC₂H₅ | CH | |
| H | CH₃ | CH₂F | CH | |
| H | OCH₃ | CH₂F | CH | |
| H | CH₃ | CH₂F | N | |
| H | OCH₃ | CH₂F | N | |

TABLE IIIb

[Structure: aziridine-N-O-SO₂-benzene(R)-SO₂NHC(O)NH-fused bicyclic heterocycle with X₁, Y₁]

| R | X₁ | Y₁ | m.p. (°C.) |
|---|---|---|---|
| H | O | CH₃ | |
| H | O | OCH₃ | |
| H | CH₂ | CH₃ | |

TABLE IIIb-continued

| R | X₁ | Y₁ | m.p. (°C.) |
|---|---|---|---|
| H | CH₂ | OCH₃ | |
| H | O | Cl | |
| 5-Cl | O | CH₃ | |
| 3-Cl | CH₂ | OCH₃ | |
| 5-CF₃ | CH₂ | CH₃ | |
| 4-CF₃ | O | CH₃ | |
| 6-Br | CH₂ | OCH₃ | |
| 4-F | O | H | |
| H | O | H | |
| 5-OCH₃ | O | OCH₃ | |

TABLE IIIc

[Structure: benzene(R) with SO₂N(aziridine) and SO₂NHC(O)NH-triazole with Y₂, X₂]

| R | Y₂ | X₂ |
|---|---|---|
| H | CH₃ | SCH₃ |
| H | CH₂CF₃ | SCH₃ |
| H | CH₃ | OCH₃ |
| H | C₂H₅ | SCH₃ |
| H | C₂H₅ | CH₃ |
| H | C₂H₅ | OCH₃ |
| H | CH₃ | CH₃ |
| H | CH₂CF₃ | OCH₃ |
| 6-Cl | CH₃ | OCH₃ |
| 5-Cl | CH₃ | OCH₃ |
| 4-Cl | CH₃ | OCH₃ |
| 5-Br | CH₃ | OCH₃ |
| 4-Br | CH₃ | OCH₃ |
| 4-F | CH₃ | OCH₃ |
| 3-F | CH₃ | OCH₃ |
| 6-OCH₃ | CH₃ | OCH₃ |
| 5-OCH₃ | CH₃ | OCH₃ |
| 4-OCH₃ | CH₃ | OCH₃ |
| 6-CF₃ | CH₃ | OCH₃ |
| 5-CF₃ | CH₃ | OCH₃ |

TABLE IIId

[Structure: benzene(R) with SO₂N(aziridine) and SO₂NHC(O)NH-furopyrimidine with Y₁, Y₃]

| R | Y₁ | Y₃ | m.p. (°C.) |
|---|---|---|---|
| H | CH₃ | H | |
| H | OCH₃ | CH₃ | |
| H | Cl | CH₃ | |
| 5-Cl | OCH₃ | H | |
| 4-Cl | OCH₃ | CH₃ | |
| 5-Br | OCH₃ | CH₃ | |
| 4-Br | CH₃ | CH₃ | |
| 4-F | OCH₃ | H | |
| 3-F | CH₃ | CH₃ | |

TABLE IIId-continued

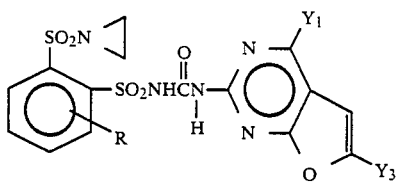

| R | Y₁ | Y₃ | m.p. (°C.) |
|---|---|---|---|
| H | H | CH₃ | |
| 5-OCH₃ | CH₃ | CH₃ | |
| 4-OCH₃ | OCH₃ | CH₃ | |
| 6-CF₃ | CH₃ | CH₃ | |
| 5-CF₃ | OCH₃ | CH₃ | |

TABLE IIIe

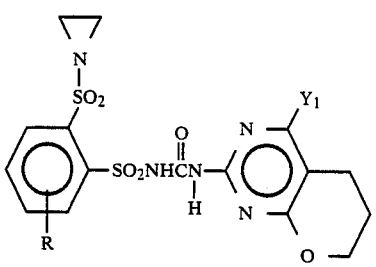

| R | Y₁ | m.p. (°C.) |
|---|---|---|
| H | CH₃ | |
| H | Cl | |
| H | OCH₃ | |
| H | H | |
| 6-Cl | CH₃ | |
| 5-Br | OCH₃ | |
| 4-Cl | OCH₃ | |
| 3-F | OCH₃ | |
| 5-CH₃ | OCH₃ | |
| 4-OCH₃ | OCH₃ | |

TABLE IIIf

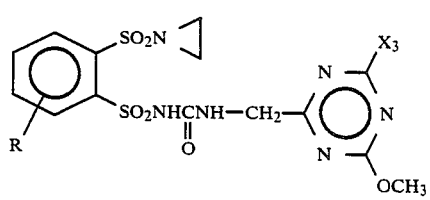

| R | X₃ | m.p. (°C.) |
|---|---|---|
| H | CH₃ | |
| H | OCH₃ | |
| 6-Cl | CH₃ | |
| 5-Br | OCH₃ | |
| 4-F | CH₃ | |
| 3-CF₃ | OCH₃ | |
| 5-CH₃ | CH₃ | |
| 4-OCH₃ | OCH₃ | |

TABLE IVa

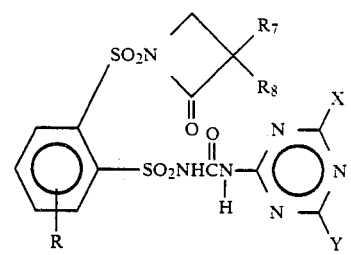

| R₇ | R₈ | R | X | Y | Z | m.p. (°C.) |
|---|---|---|---|---|---|---|
| CH₃ | CH₃ | H | CH₃ | CH₃ | CH | |
| CH₃ | CH₃ | H | OCH₃ | CH₃ | CH | |
| CH₃ | CH₃ | H | OCH₃ | OCH₃ | CH | |
| CH₃ | CH₃ | H | CH₃ | C₂H₅ | CH | |
| CH₃ | CH₃ | H | OCH₃ | C₂H₅ | CH | |
| CH₃ | CH₃ | H | CH₃ | OC₂H₅ | CH | |
| CH₃ | CH₃ | H | OCH₃ | OC₂H₅ | CH | |
| CH₃ | CH₃ | H | CH₃ | CH₂OCH₃ | CH | |
| CH₃ | CH₃ | H | OCH₃ | CH₂OCH₃ | CH | |
| CH₃ | CH₃ | H | Br | OC₂H₅ | CH | |
| CH₃ | CH₃ | H | Br | OCH₃ | CH | |
| CH₃ | CH₃ | H | OCH₃ | N(CH₃)₂ | CH | |
| CH₃ | CH₃ | H | CH₃ | CH₃ | N | |
| CH₃ | CH₃ | H | OCH₃ | CH₃ | N | |
| CH₃ | CH₃ | H | OCH₃ | OCH₃ | N | |
| H | CH₃ | H | CH₃ | C₂H₅ | N | |
| H | CH₃ | H | OCH₃ | C₂H₅ | N | |
| H | CH₃ | H | CH₃ | OC₂H₅ | N | |
| H | CH₃ | H | OCH₃ | OC₂H₅ | N | |
| H | CH₃ | H | CH₃ | CH₂OCH₃ | N | |
| H | CH₃ | H | OCH₃ | CH₂OCH₃ | N | |
| H | H | H | OCF₂H | OCH₃ | N | |
| H | H | H | OCH₂CH₃ | OCH₃ | N | |
| H | H | H | OCH₃ | N(CH₃)₂ | N | |
| H | H | H | CH₃ | CH(OCH₃)₂ | CH | |
| CH₃ | CH₃ | H | OCH₃ | CH(OCH₃)₂ | CH | |
| CH₃ | CH₃ | H | CH₃ | 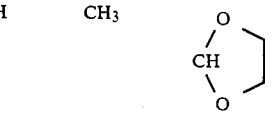 | | |
| CH₃ | CH₃ | H | OCH₃ | 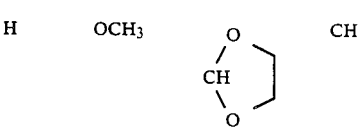 | CH | |
| CH₃ | CH₃ | H | CH₃ | CH(OCH₃)₂ | N | |
| CH₃ | CH₃ | H | OCH₃ | CH(OCH₃)₂ | N | |
| CH₃ | CH₃ | H | CH₃ | 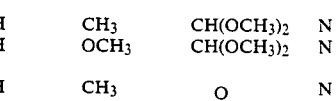 | N | |
| CH₃ | CH₃ | H | OCH₃ | 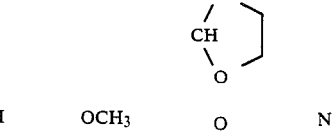 | N | |
| CH₃ | CH₃ | H | Cl | OCH₃ | CH | |
| CH₃ | CH₃ | H | Cl | OC₂H₅ | CH | |
| CH₃ | CH₃ | H | Cl | NHCH₃ | CH | |
| CH₃ | CH₃ | H | Cl | N(CH₃)₂ | CH | |
| CH₃ | CH₃ | H | CH₃ | SCH₃ | N | |
| CH₃ | CH₃ | H | OCH₃ | SCH₃ | N | |
| CH₃ | CH₃ | H | CH₃ | SCH₃ | CH | |
| CH₃ | CH₃ | H | OCH₃ | SCH₃ | CH | |
| CH₃ | CH₃ | 6-Cl | OCH₃ | OCH₃ | CH | |
| CH₃ | CH₃ | 6-Cl | OCH₃ | N(CH₃)₂ | CH | |
| CH₃ | CH₃ | 5-Cl | CH₃ | OCH₃ | CH | |

TABLE IVa-continued

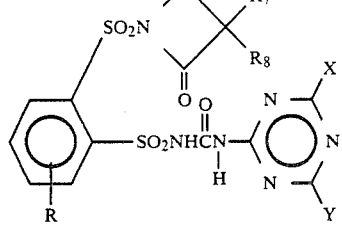

| R7 | R8 | R | X | Y | Z | m.p. (°C.) |
|---|---|---|---|---|---|---|
| CH3 | CH3 | 5-Cl | CH3 | CH3 | CH | |
| CH3 | CH3 | 4-Cl | CH3 | N(CH3)2 | CH | |
| CH3 | CH3 | 4-Cl | CH3 | CH3 | N | |
| CH3 | CH3 | 3-Cl | OCH3 | CH3 | N | |
| CH3 | CH3 | 3-Cl | OCH3 | OCH3 | N | |
| CH3 | CH3 | 6-Br | CH3 | C2H5 | N | |
| CH3 | CH3 | 6-Br | OCH3 | C2H5 | N | |
| CH3 | CH3 | 5-Br | CH3 | OC2H5 | N | |
| CH3 | CH3 | 5-Br | OCH3 | OC2H5 | N | |
| CH3 | CH3 | 4-Br | CH3 | CH2OCH3 | N | |
| CH3 | CH3 | 3-Br | OCH3 | CH2OCH3 | N | |
| CH3 | CH3 | 6-F | OCH3 | OCH3 | N | |
| CH3 | CH3 | 5-F | OCH3 | CH3 | N | |
| CH3 | CH3 | 4-F | OCH3 | N(CH3)2 | N | |
| CH3 | CH3 | 3-F | CH3 | dioxolane | CH | |
| CH3 | CH3 | 6-OCH3 | OCH3 | dioxolane | CH | |
| CH3 | H | 5-OCH3 | CH3 | dioxolane | N | |
| CH3 | H | 5-OCH3 | OCH3 | dioxolane | N | |
| CH3 | H | 4-OCH3 | Cl | OCH3 | CH | |
| CH3 | H | 3-OCH3 | CH3 | CH3 | CH | |
| H | H | 6-CF3 | OCH3 | CH3 | CH | |
| H | H | 5-CF3 | OCH3 | OCH3 | CH | |
| H | H | 4-CF3 | CH3 | C2H5 | CH | |
| H | H | 4-CF3 | OCH3 | C2H5 | CH | |
| H | H | 3-CF3 | CH3 | OC2H5 | CH | |
| H | H | H | OCH3 | CH2F | CH | |
| H | H | H | CH3 | CH2F | CH | |
| H | H | H | OCH3 | CH2F | N | |
| H | H | H | CH3 | CH2F | N | |
| H | H | H | CH3 | NHCH3 | CH | |
| H | H | H | OCH3 | NHCH3 | CH | |
| H | H | H | CH3 | NHCH3 | N | |
| H | H | H | OCH3 | NHCH3 | N | |

TABLE IVb

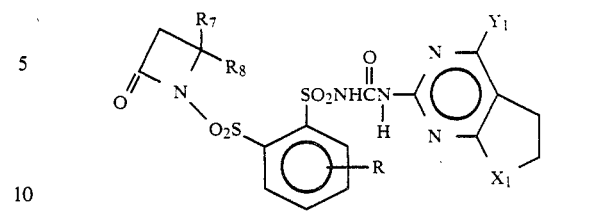

| R | R7 | R8 | X1 | Y1 | m.p. (°C.) |
|---|---|---|---|---|---|
| H | CH3 | CH3 | O | CH3 | |
| H | CH3 | CH3 | O | OCH3 | |
| H | CH3 | CH3 | CH2 | CH3 | |
| H | CH3 | H | CH2 | OCH3 | |
| H | CH3 | CH3 | O | Cl | |
| 5-Cl | CH3 | CH3 | O | CH3 | |
| 3-Cl | CH3 | CH3 | CH2 | OCH3 | |
| 5-CF3 | CH3 | CH3 | CH2 | CH3 | |
| 4-CF3 | CH3 | CH3 | O | CH3 | |
| 6-Br | CH3 | CH3 | CH2 | OCH3 | |
| 4-F | CH3 | CH3 | O | H | |
| H | H | H | O | H | |
| 5-OCH3 | H | H | O | OCH3 | |

TABLE IVc

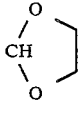

| R | R7 | R8 | Y2 | X2 |
|---|---|---|---|---|
| H | CH3 | CH3 | CH3 | SCH3 |
| H | CH3 | CH3 | CH2CF3 | SCH3 |
| H | CH3 | CH3 | CH3 | OCH3 |
| H | CH3 | CH3 | C2H5 | SCH3 |
| H | CH3 | CH3 | C2H5 | CH3 |
| H | CH3 | CH3 | C2H5 | OCH3 |
| H | H | H | CH3 | CH3 |
| H | H | H | CH2CF3 | OCH3 |
| 6-Cl | CH3 | CH3 | CH3 | OCH3 |
| 5-Cl | CH3 | CH3 | CH3 | OCH3 |
| 4-Cl | CH3 | CH3 | CH3 | OCH3 |
| 5-Br | CH3 | CH3 | CH3 | OCH3 |
| 4-Br | CH3 | CH3 | CH3 | OCH3 |
| 4-F | CH3 | CH3 | CH3 | OCH3 |
| 3-F | CH3 | CH3 | CH3 | OCH3 |
| 6-OCH3 | CH3 | CH3 | CH3 | OCH3 |
| 5-OCH3 | CH3 | CH3 | CH3 | OCH3 |
| 4-OCH3 | CH3 | H | CH3 | OCH3 |
| 6-CF3 | CH3 | H | CH3 | OCH3 |
| 5-CF3 | H | H | CH3 | OCH3 |

TABLE IVd

| R | R7 | R8 | Y1 | Y3 | m.p. (°C.) |
|---|-----|-----|------|------|------------|
| H | CH3 | CH3 | CH3 | H | |
| H | CH3 | CH3 | OCH3 | CH3 | |
| H | CH3 | CH3 | Cl | CH3 | |
| 5-Cl | CH3 | CH3 | OCH3 | H | |
| 4-Cl | CH3 | CH3 | CH3 | CH3 | |
| 5-Br | CH3 | CH3 | OCH3 | CH3 | |
| 4-Br | CH3 | CH3 | CH3 | CH3 | |
| 4-F | CH3 | CH3 | OCH3 | H | |
| 3-F | CH3 | CH3 | CH3 | CH3 | |
| H | CH3 | CH3 | H | CH3 | |
| 5-OCH3 | CH3 | CH3 | CH3 | CH3 | |
| 4-OCH3 | CH3 | CH3 | OCH3 | CH3 | |
| 6-CF3 | CH3 | H | CH3 | CH3 | |
| 5-CF3 | H | H | OCH3 | CH3 | |

TABLE IVe

| R | R7 | R8 | Y | m.p. (°C.) |
|---|-----|-----|------|------------|
| H | CH3 | CH3 | CH3 | |
| H | CH3 | CH3 | Cl | |
| H | CH3 | CH3 | OCH3 | |
| H | CH3 | H | H | |

TABLE IVe-continued

| R | R7 | R8 | Y | m.p. (°C.) |
|---|-----|-----|------|------------|
| 6-Cl | CH3 | CH3 | CH3 | |
| 5-Br | CH3 | CH3 | OCH3 | |
| 4-CH3 | CH3 | CH3 | OCH3 | |
| 3-CF3 | CH3 | CH3 | OCH3 | |
| 5-F | CH3 | CH3 | OCH3 | |
| 4-OCH3 | H | H | OCH3 | |

TABLE IVf

| R | R7 | R8 | X3 | m.p. (°C.) |
|---|-----|-----|------|------------|
| H | CH3 | CH3 | CH3 | |
| H | CH3 | CH3 | OCH3 | |
| 6-Cl | CH3 | CH3 | CH3 | |
| 5-Br | CH3 | CH3 | OCH3 | |
| 4-F | CH3 | CH3 | CH3 | |
| 3-CF3 | CH3 | CH3 | OCH3 | |
| 5-CH3 | CH3 | CH3 | CH3 | |
| 4-OCH3 | CH3 | CH3 | OCH3 | |
| H | H | CH3 | CH3 | |
| H | H | H | CH3 | |

TABLE Va

| R1 | R | X | Y | Z | m.p. (°C.) |
|----|---|------|------|----|------------|
| H | H | CH3 | CH3 | CH | |
| H | H | OCH3 | CH3 | CH | 154–155° C.(d) |
| H | H | OCH3 | OCH3 | CH | 192–195° C.(d) |
| H | H | CH3 | C2H5 | CH | |
| H | H | OCH3 | C2H5 | CH | |
| H | H | CH3 | OC2H5 | CH | |
| H | H | OCH3 | OC2H5 | CH | |
| H | H | CH3 | CH2OCH3 | CH | |
| H | H | OCH3 | CH2OCH3 | CH | |
| H | H | Br | OC2H5 | CH | |
| H | H | Br | OCH3 | CH | |
| H | H | OCH3 | N(CH3)2 | CH | |
| H | H | CH3 | CH3 | N | |

TABLE Va-continued

[Structure: benzene ring with SO₂N(R₁)-H group and SO₂NHC(O)NH-pyrimidine/triazine group with X, Y, Z substituents; R on benzene ring]

| R₁ | R | X | Y | Z | m.p. (°C.) |
|---|---|---|---|---|---|
| H | H | OCH₃ | CH₃ | N | |
| H | H | OCH₃ | OCH₃ | N | 120° C.(d) |
| H | H | CH₃ | C₂H₅ | N | |
| H | H | OCH₃ | C₂H₅ | N | |
| H | H | CH₃ | OC₂H₅ | N | |
| H | H | OCH₃ | OC₂H₅ | N | |
| H | H | CH₃ | CH₂OCH₃ | N | |
| H | H | OCH₃ | CH₂OCH₃ | N | |
| H | H | OCF₂H | OCH₃ | N | |
| H | H | OCH₂CH₃ | OCH₃ | N | |
| H | H | OCH₃ | N(CH₃)₂ | N | |
| H | H | CH₃ | CH(OCH₃)₂ | CH | |
| H | H | OCH₃ | CH(OCH₃)₂ | CH | |
| H | H | CH₃ | —OCH₂CH₂O—CH (dioxolane) | CH | |
| H | H | OCH₃ | —OCH₂CH₂O—CH (dioxolane) | CH | |
| H | H | CH₃ | CH(OCH₃)₂ | N | |
| H | H | OCH₃ | CH(OCH₃)₂ | N | |
| H | H | CH₃ | —OCH₂CH₂O—CH (dioxolane) | N | |
| H | H | OCH₃ | —OCH₂CH₂O—CH (dioxolane) | N | |
| H | H | Cl | OCH₃ | CH | |
| H | H | Cl | OC₂H₅ | CH | |
| H | H | Cl | NHCH₃ | CH | |
| H | H | Cl | N(CH₃)₂ | CH | |
| H | H | CH₃ | SCH₃ | N | |
| H | H | OCH₃ | SCH₃ | N | |
| H | H | CH₃ | SCH₃ | CH | |
| H | H | OCH₃ | SCH₃ | CH | |
| H | 6-Cl | OCH₃ | OCH₃ | CH | |
| H | 6-Cl | OCH₃ | N(CH₃)₂ | CH | |
| H | 5-Cl | CH₃ | OCH₃ | CH | |
| H | 5-Cl | CH₃ | CH₃ | CH | |
| H | 4-Cl | CH₃ | N(CH₃)₂ | CH | |
| H | 4-Cl | CH₃ | CH₃ | N | |
| H | 3-Cl | OCH₃ | CH₃ | N | |
| H | 3-Cl | OCH₃ | OCH₃ | N | |
| H | 6-Br | CH₃ | C₂H₅ | N | |
| H | 6-Br | OCH₃ | C₂H₅ | N | |
| H | 5-Br | CH₃ | OC₂H₅ | N | |
| H | 5-Br | OCH₃ | OC₂H₅ | N | |
| H | 4-Br | CH₃ | CH₂OCH₃ | N | |
| H | 3-Br | OCH₃ | CH₂OCH₃ | N | |
| H | H | CH₃ | —NHCH₃ | CH | |
| H | H | OCH₃ | —NHCH₃ | CH | |
| H | H | CH₃ | —NHCH₃ | N | |
| H | H | OCH₃ | —NHCH₃ | N | |
| H | 6-F | OCH₃ | OCH₃ | N | |
| H | 5-F | OCH₃ | CH₃ | N | |

TABLE Va-continued

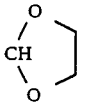

| R₁ | R | X | Y | Z | m.p. (°C.) |
|---|---|---|---|---|---|
| H | 4-F | OCH₃ | N(CH₃)₂ | N | |
| H | 3-F | CH₃ | $\overset{O}{\underset{O}{\overset{|}{\underset{|}{CH}}}}$ (methylenedioxy) | CH | |
| H | 6-OCH₃ | OCH₃ | $\overset{O}{\underset{O}{\overset{|}{\underset{|}{CH}}}}$ | CH | |
| H | 5-OCH₃ | CH₃ | $\overset{O}{\underset{O}{\overset{|}{\underset{|}{CH}}}}$ | N | |
| H | 5-OCH₃ | OCH₃ | $\overset{O}{\underset{O}{\overset{|}{\underset{|}{CH}}}}$ | N | |
| H | 4-OCH₃ | Cl | OCH₃ | CH | |
| H | 3-OCH₃ | CH₃ | CH₃ | CH | |
| H | 6-CF₃ | OCH₃ | CH₃ | CH | |
| H | 5-CF₃ | OCH₃ | OCH₃ | CH | |
| H | 4-CF₃ | CH₃ | C₂H₅ | CH | |
| H | 4-CF₃ | OCH₃ | C₂H₅ | CH | |
| H | 3-CF₃ | CH₃ | OC₂H₅ | CH | |
| $\overset{O}{\underset{}{\overset{\|}{C}}}CH_3$ | H | CH₃ | CH₃ | CH | |
| $\overset{O}{\underset{}{\overset{\|}{C}}}CH_3$ | H | OCH₃ | CH₃ | CH | |
| $\overset{O}{\underset{}{\overset{\|}{C}}}CH_2CH_3$ | H | OCH₃ | OCH₃ | CH | |
| $\overset{O}{\underset{}{\overset{\|}{C}}}CH_2CH_2CH_3$ | H | CH₃ | C₂H₅ | CH | |
| $\overset{O}{\underset{}{\overset{\|}{C}}}CF_3$ | H | OCH₃ | C₂H₅ | CH | |
| $\overset{O}{\underset{}{\overset{\|}{C}}}Ph$ | H | CH₃ | OC₂H₅ | CH | |
| $\overset{O}{\underset{}{\overset{\|}{CO}}}CH_3$ | H | OCH₃ | OC₂H₅ | CH | |
| $\overset{O}{\underset{}{\overset{\|}{CO}}}CH_2CH_3$ | H | CH₃ | CH₂OCH₃ | CH | |
| $\overset{O}{\underset{}{\overset{\|}{CO}}}(CH_2)_3CH_3$ | H | OCH₃ | CH₂OCH₃ | CH | |

TABLE Va-continued

| R₁ | R | X | Y | Z | m.p. (°C.) |
|---|---|---|---|---|---|
| $\underset{CO(CH_2)_3CH_3}{\overset{O}{\|}}$ | H | Br | OC₂H₅ | CH | |
| $\underset{CNH_2}{\overset{O}{\|}}$ | H | Br | OCH₃ | CH | |
| $\underset{CNH_2}{\overset{O}{\|}}$ | H | OCH₃ | N(CH₃)₂ | CH | |
| $\underset{CNHCH_3}{\overset{O}{\|}}$ | H | CH₃ | CH₃ | N | |
| $\underset{CNHCH_2CH_3}{\overset{O}{\|}}$ | H | OCH₃ | CH₃ | N | |
| $\underset{CNH(CH_2)_3CH_3}{\overset{O}{\|}}$ | H | OCH₃ | OCH₃ | N | |
| $\underset{CNHPh}{\overset{O}{\|}}$ | H | CH₃ | C₂H₅ | N | |
| $\underset{CN(CH_3)_2}{\overset{O}{\|}}$ | H | OCH₃ | C₂H₅ | N | |
| $\underset{CN(CH_3)CH_2CH_3}{\overset{O}{\|}}$ | H | CH₃ | OC₂H₅ | N | |
| $\underset{CN(CH_3)Ph}{\overset{O}{\|}}$ | H | OCH₃ | OC₂H₅ | N | |
| $\underset{CN(CH_2CH_3)_2}{\overset{O}{\|}}$ | H | CH₃ | CH₂OCH₃ | N | |
| $\underset{CN(CH_2CH_3)Ph}{\overset{O}{\|}}$ | H | OCH₃ | CH₂OCH₃ | N | |
| 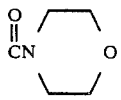 | H | OCF₂H | OCH₃ | N | |
|  | H | OCH₂CH₃ | OCH₃ | N | |
|  | H | OCH₃ | N(CH₃)₂ | N | |
| $\underset{CN(CH_2CH_2CH_3)_2}{\overset{O}{\|}}$ | H | CH₃ | CH(OCH₃)₂ | CH | |

TABLE Va-continued $$\text{structure with } R_1\text{SO}_2\text{N-H, SO}_2\text{NHCNH(C=O)-triazine/pyrimidine with X, Y, Z, R substituents}$$

| R₁ | R | X | Y | Z | m.p. (°C.) |
|---|---|---|---|---|---|
| COCH₃ | 6-Cl | OCH₃ | OCH₃ | CH | |
| COCH₃ | 6-Cl | OCH₃ | N(CH₃)₂ | CH | |
| COCH₂CH₃ | 5-Cl | CH₃ | OCH₃ | CH | |
| COCH₂CH₂CH₃ | 5-Cl | CH₃ | CH₃ | CH | |
| COCF₃ | 4-Cl | CH₃ | N(CH₃)₂ | CH | |
| COPh | 4-Cl | CH₃ | CH₃ | N | |
| COOCH₃ | 3-Cl | OCH₃ | CH₃ | N | |
| COOCH₂CH₃ | 3-Cl | OCH₃ | OCH₃ | N | |
| COCH₃ | 6-Br | CH₃ | C₂H₅ | N | |
| COO(CH₂)₃CH₃ | 6-Br | OCH₃ | C₂H₅ | N | |
| CONH₂ | 5-Br | CH₃ | OC₂H₅ | N | |
| CONHCH₃ | 5-Br | OCH₃ | OC₂H₅ | N | |
| CONH₂ | 4-Br | CH₃ | CH₂OCH₃ | N | |
| CONHCH₂CH₃ | 3-Br | OCH₃ | CH₂OCH₃ | N | |
| CONH(CH₂)₃CH₃ | 6-F | OCH₃ | OCH₃ | N | |
| CONHPh | 5-F | OCH₃ | CH₃ | N | |
| CON(CH₃)₂ | 4-F | OCH₃ | N(CH₃)₂ | N | |

TABLE Va-continued

![structure]

| R₁ | R | X | Y | Z | m.p. (°C.) |
|---|---|---|---|---|---|
| $\underset{\text{CN(CH}_3\text{)CH}_2\text{CH}_3}{\overset{\text{O}}{\|}}$ | 3-F | CH₃ | ⟨OCH(O)O⟩ (1,3-dioxolan-2-yl) | CH | |
| $\underset{\text{CN(CH}_3\text{)Ph}}{\overset{\text{O}}{\|}}$ | 6-OCH₃ | OCH₃ | ⟨OCH(O)O⟩ | CH | |
| $\underset{\text{CN(CH}_2\text{CH}_3\text{)}_2}{\overset{\text{O}}{\|}}$ | 5-OCH₃ | CH₃ | ⟨OCH(O)O⟩ | N | |
| $\underset{\text{CN(CH}_2\text{CH}_3\text{)Ph}}{\overset{\text{O}}{\|}}$ | 5-OCH₃ | OCH₃ | ⟨OCH(O)O⟩ | N | |
| $\underset{\text{CN}}{\overset{\text{O}}{\|}}$〈piperidyl〉 | 4-OCH₃ | Cl | OCH₃ | CH | |
| $\underset{\text{CN}}{\overset{\text{O}}{\|}}$〈pyrrolidyl〉 | 3-OCH₃ | CH₃ | CH₃ | CH | |
| $\underset{\text{CN}}{\overset{\text{O}}{\|}}$〈morpholinyl〉 | 6-CF₃ | OCH₃ | CH₃ | CH | |
| $\underset{\text{CCH}_3}{\overset{\text{O}}{\|}}$ | 5-CF₃ | OCH₃ | OCH₃ | CH | |
| $\underset{\text{CCH}_2\text{CH}_3}{\overset{\text{O}}{\|}}$ | 4-CF₃ | CH₃ | C₂H₅ | CH | |
| $\underset{\text{COCH}_3}{\overset{\text{O}}{\|}}$ | 4-CF₃ | OCH₃ | C₂H₅ | CH | |
| $\underset{\text{CNH}_2}{\overset{\text{O}}{\|}}$ | 3-CF₃ | CH₃ | OC₂H₅ | CH | |
| H | H | CH₃ | CH₂F | CH | |
| H | H | OCH₃ | CH₂F | CH | |
| H | H | CH₃ | CH₂F | N | |
| H | H | OCH₃ | CH₂F | N | |
| CF₂H | H | OCH₃ | CH₃ | CH | |
| CF₂H | H | CH₃ | CH₃ | CH | |
| CF₂H | H | OCH₃ | CH₃ | N | |
| CF₂H | H | OCH₃ | OCH₃ | N | |

TABLE Vb

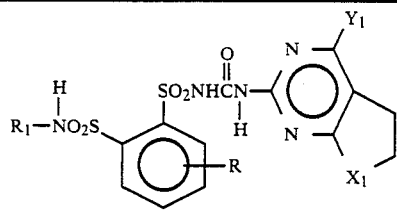

| R | R₁ | X₁ | Y₁ | m.p. (°C.) |
|---|---|---|---|---|
| H | H | O | CH₃ | |
| H | H | O | OCH₃ | |
| H | H | CH₂ | CH₃ | |
| H | H | CH₂ | OCH₃ | |
| H | H | O | Cl | |
| 5-Cl | H | O | CH₃ | |
| 3-Cl | H | CH₂ | OCH₃ | |
| 5-CF₃ | H | CH₂ | CH₃ | |
| 4-CF₃ | H | O | CH₃ | |
| 6-Br | H | CH₂ | OCH₃ | |
| 4-F | H | O | H | |
| H | H | O | H | |
| 5-OCH₃ | H | O | OCH₃ | |
| H | $\overset{O}{\underset{\|}{C}}CH_3$ | O | CH₃ | |
| H | $\overset{O}{\underset{\|}{C}}CF_3$ | O | OCH₃ | |
| H | $\overset{O}{\underset{\|}{C}}OCH_3$ | CH₂ | CH₃ | |
| H | (piperidinyl carbonyl) | CH₂ | OCH₃ | |
| H | $\overset{O}{\underset{\|}{C}}CH_3$ | O | Cl | |
| 5-Cl | $\overset{O}{\underset{\|}{C}}CF_3$ | O | CH₃ | |
| 3-Cl | $\overset{O}{\underset{\|}{C}}NH_2$ | CH₂ | OCH₃ | |
| 5-CF₃ | $\overset{O}{\underset{\|}{C}}OCH_2CH_3$ | CH₂ | CH₃ | |
| 4-CF₃ | $\overset{O}{\underset{\|}{C}}NHCH_2CH_3$ | O | CH₃ | |
| 6-Br | $\overset{O}{\underset{\|}{C}}N(CH_3)_2$ | CH₂ | OCH₃ | |
| 4-F | (morpholinyl carbonyl) | O | H | |
| H | $\overset{O}{\underset{\|}{C}}CH_2CH_3$ | O | H | |
| 5-OCH₃ | $\overset{O}{\underset{\|}{C}}NH_2$ | O | OCH₃ | |
| H | CF₂H | CH₂ | OCH₃ | |

TABLE Vb-continued

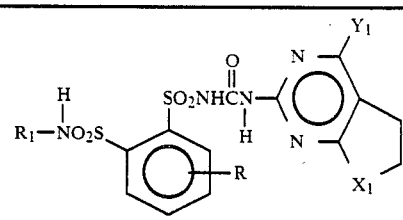

| R | R₁ | X₁ | Y₁ | m.p. (°C.) |
|---|---|---|---|---|
| H | CF₂H | O | CH₃ | |

TABLE Vc

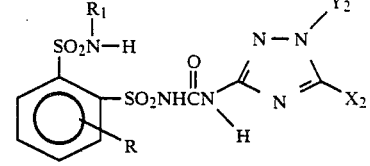

| R | R₁ | Y₂ | X₂ |
|---|---|---|---|
| H | H | CH₃ | SCH₃ |
| H | H | CH₂CF₃ | SCH₃ |
| H | H | CH₃ | OCH₃ |
| H | H | C₂H₅ | SCH₃ |
| H | H | C₂H₅ | CH₃ |
| H | H | C₂H₅ | OCH₃ |
| H | H | CH₃ | CH₃ |
| H | H | CH₂CF₃ | OCH₃ |
| 6-Cl | H | CH₃ | OCH₃ |
| 5-Cl | H | CH₃ | OCH₃ |
| 4-Cl | H | CH₃ | OCH₃ |
| 5-Br | H | CH₃ | OCH₃ |
| 4-Br | H | CH₃ | OCH₃ |
| 4-F | H | CH₃ | OCH₃ |
| 3-F | H | CH₃ | OCH₃ |
| 6-OCH₃ | H | CH₃ | OCH₃ |
| 5-OCH₃ | H | CH₃ | OCH₃ |
| 4-OCH₃ | H | CH₃ | OCH₃ |
| 6-CF₃ | H | CH₃ | OCH₃ |
| 5-CF₃ | H | CH₃ | OCH₃ |
| H | $\overset{O}{\underset{\|}{C}}CH_3$ | CH₃ | SCH₃ |
| H | $\overset{O}{\underset{\|}{C}}CF_3$ | CH₂CF₃ | SCH₃ |
| H | $\overset{O}{\underset{\|}{C}}OCH_3$ | CH₃ | OCH₃ |
| H | $\overset{O}{\underset{\|}{C}}CH_3$ | C₂H₅ | SCH₃ |
| H | $\overset{O}{\underset{\|}{C}}CF_3$ | C₂H₅ | CH₃ |
| H | $\overset{O}{\underset{\|}{C}}NH_2$ | C₂H₅ | OCH₃ |
| H | $\overset{O}{\underset{\|}{C}}N(CH_3)_2$ | CH₃ | CH₃ |
| H | $\overset{O}{\underset{\|}{C}}NHCH_2CH_3$ | CH₂CF₃ | OCH₃ |

TABLE Vc-continued

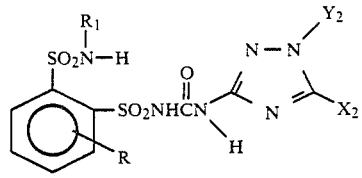

| R | R1 | Y2 | X2 |
|---|---|---|---|
| 6-Cl | COCH3 | CH3 | OCH3 |
| 5-Cl | COCH3 | CH3 | OCH3 |
| 4-Cl | COCF3 | CH3 | OCH3 |
| 5-Br | COCH3 | CH3 | OCH3 |
| 4-Br | CONH2 | CH3 | OCH3 |
| 4-F | COCF3 | CH3 | OCH3 |
| 3-F | COCH3 | CH3 | OCH3 |
| 6-OCH3 | COCH2CH3 | CH3 | OCH3 |
| 5-OCH3 | CON(CH3)2 | CH3 | OCH3 |
| 4-OCH3 | COCH3 | CH3 | OCH3 |
| 6-CF3 | COCF3 | CH3 | OCH3 |
| 5-CF3 | COCH2CH3 | CH3 | OCH3 |
| H | CF2H | CH3 | OCH3 |
| H | CF2H | CH3 | OCH3 |

TABLE Vd

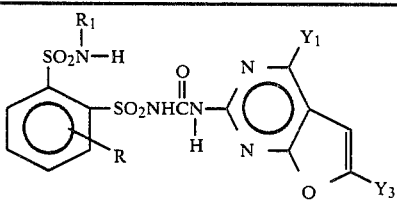

| R | R1 | Y1 | Y3 | m.p. (°C.) |
|---|---|---|---|---|
| H | H | CH3 | H | |
| H | H | OCH3 | CH3 | |
| H | H | Cl | CH3 | |
| 5-Cl | H | OCH3 | H | |
| 4-Cl | H | CH3 | CH3 | |
| 5-Br | H | OCH3 | CH3 | |
| 4-Br | H | CH3 | CH3 | |

TABLE Vd-continued

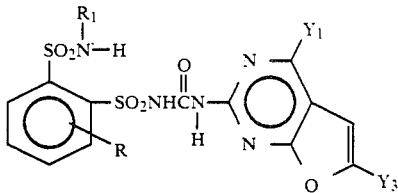

| R | R1 | Y1 | Y3 | m.p. (°C.) |
|---|---|---|---|---|
| 4-F | H | OCH3 | H | |
| 3-F | H | CH3 | CH3 | |
| H | H | H | CH3 | |
| 5-OCH3 | H | CH3 | H | |
| 4-OCH3 | H | OCH3 | CH3 | |
| 6-CF3 | H | CH3 | CH3 | |
| 5-CF3 | H | OCH3 | CH3 | |
| H | COCH3 | CH3 | CH3 | |
| H | COCH2CH3 | OCH3 | H | |
| H | COCF3 | Cl | CH3 | |
| 5-Cl | CONH2 | OCH3 | CH3 | |
| 4-Cl | CONHCH3 | CH3 | CH3 | |
| 5-Br | CONHCH2CH3 | OCH3 | H | |
| 4-Br | CON(pyrrolidine) | CH3 | CH3 | |
| 4-F | COCH3 | OCH3 | CH3 | |
| 3-F | COCF3 | CH3 | CH3 | |
| H | COCH3 | H | CH3 | |
| 5-OCH3 | CON(morpholine) | CH3 | CH3 | |
| 4-OCH3 | COCH3 | OCH3 | H | |
| 6-CF3 | COCH3 | CH3 | CH3 | |
| 5-CF3 | COCF3 | OCH3 | CH3 | |
| H | CF2H | OCH3 | H | |
| H | CF2H | CH3 | CH3 | |

TABLE Ve

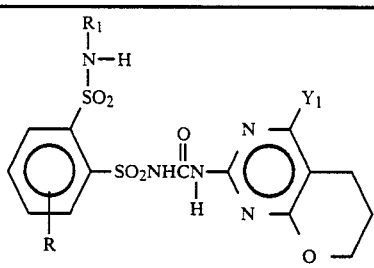

| R | R₁ | Y₁ | m.p. (°C.) |
|---|---|---|---|
| H | H | CH₃ | |
| H | H | Cl | |
| H | H | OCH₃ | |
| H | H | H | |
| 6-Cl | H | CH₃ | |
| 5-Br | H | OCH₃ | |
| 4-CH₃ | H | OCH₃ | |
| 3-CF₃ | H | OCH₃ | |
| 5-F | H | OCH₃ | |
| 4-OCH₃ | H | OCH₃ | |
| H | $\underset{CCH_3}{\overset{O}{\|}}$ | CH₃ | |
| H | $\underset{CCH_3}{\overset{O}{\|}}$ | OCH₃ | |
| H | $\underset{CN(CH_3)_2}{\overset{O}{\|}}$ | H | |
| H | $\underset{CNH_2}{\overset{O}{\|}}$ | OCH₃ | |
| 6-Cl | $\underset{CCH_3}{\overset{O}{\|}}$ | CH₃ | |
| 5-Br | $\underset{CCH_3}{\overset{O}{\|}}$ | OCH₃ | |
| 3-CH₃ | $\underset{CCH_3}{\overset{O}{\|}}$ | OCH₃ | |
| 6-CF₃ | $\underset{CCH_3}{\overset{O}{\|}}$ | OCH₃ | |
| 5-F | $\underset{CCH_3}{\overset{O}{\|}}$ | OCH₃ | |

TABLE Ve-continued

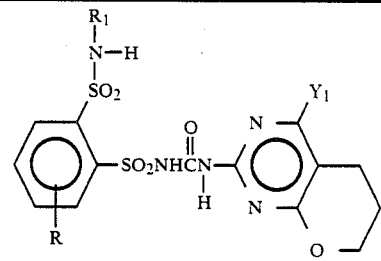

| R | R₁ | Y₁ | m.p. (°C.) |
|---|---|---|---|
| 4-OCH₃ | $\underset{COCH_2CH_3}{\overset{O}{\|}}$ | OCH₃ | |
| H | CF₂H | OCH₃ | |
| H | CF₂H | CH₃ | |

TABLE Vf

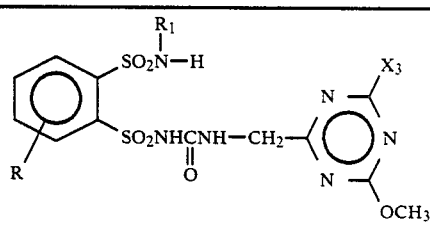

| R | R₁ | X₃ | m.p. (°C.) |
|---|---|---|---|
| H | H | CH₃ | |
| H | H | OCH₃ | |
| 6-Cl | H | CH₃ | |
| 5-Br | H | OCH₃ | |
| 4-F | H | CH₃ | |
| 3-CF₃ | H | OCH₃ | |
| 5-CH₃ | H | CH₃ | |
| 4-OCH₃ | H | OCH₃ | |
| H | $\underset{CCH_3}{\overset{O}{\|}}$ | CH₃ | |
| H | $\underset{COCH_2CH_3}{\overset{O}{\|}}$ | CH₃ | |
| 6-Cl | $\underset{CCH_3}{\overset{O}{\|}}$ | OCH₃ | |
| H | CF₂H | OCH₃ | |

TABLE VIa

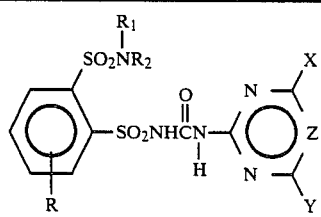

| R₁ | R | R₂ | X | Y | Z | m.p. (°C.) |
|---|---|---|---|---|---|---|
| $\underset{CCH_3}{\overset{O}{\|}}$ | H | CH₃ | CH₃ | CH₃ | CH | |

TABLE VIa-continued

Structure: benzene ring with SO₂NR₂ (with R₁ on N) and SO₂NHC(O)NH— linked to pyrimidine/triazine ring bearing X, Y, Z; R on benzene ring.

| R₁ | R | R₂ | X | Y | Z | m.p. (°C.) |
|---|---|---|---|---|---|---|
| O‖CCH₃ | H | CH₃ | OCH₃ | CH₃ | CH | |
| O‖CCH₂CH₃ | H | CH₃ | OCH₃ | OCH₃ | CH | |
| O‖CCH₂CH₂CH₃ | H | CH₃ | CH₃ | C₂H₅ | CH | |
| O‖CCF₃ | H | CH₃ | OCH₃ | C₂H₅ | CH | |
| O‖CPh | H | C₂H₅ | CH₃ | OC₂H₅ | CH | |
| O‖COCH₃ | H | CH₃ | OCH₃ | OC₂H₅ | CH | |
| O‖COCH₂CH₃ | H | CH₃ | CH₃ | CH₂OCH₃ | CH | |
| O‖CO(CH₂)₃CH₃ | H | CH₃ | OCH₃ | CH₂OCH₃ | CH | |
| O‖CO(CH₂)₃CH₃ | H | CH₃ | Br | OC₂H₅ | CH | |
| O‖CNH₂ | H | CH₃ | Br | OCH₃ | CH | |
| O‖CNH₂ | H | n-C₃H₇ | OCH₃ | N(CH₃)₂ | CH | |
| O‖CNHCH₃ | H | CH₃ | CH₃ | CH₃ | N | |
| O‖CNHCH₂CH₃ | H | CH₃ | OCH₃ | CH₃ | N | |
| O‖CNH(CH₂)₃CH₃ | H | CH₃ | OCH₃ | OCH₃ | N | |
| O‖CNHPh | H | CH₃ | CH₃ | C₂H₅ | N | |
| O‖CN(CH₃)₂ | H | CH₃ | OCH₃ | C₂H₅ | N | |
| O‖CN(CH₃)CH₂CH₃ | H | CH₃ | CH₃ | OC₂H₅ | N | |
| O‖CN(CH₃)Ph | H | CH₃ | OCH₃ | OC₂H₅ | N | |

TABLE VIa-continued

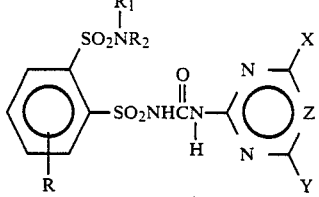

| R₁ | R | R₂ | X | Y | Z | m.p. (°C.) |
|---|---|---|---|---|---|---|
| O=CN(CH₂CH₃)₂ | H | i-C₃H₇ | CH₃ | CH₂OCH₃ | N | |
| O=CN(CH₂CH₃)Ph | H | CH₃ | OCH₃ | CH₂OCH₃ | N | |
| O=CN (piperidinyl) | H | CH₃ | OCF₂H | OCH₃ | N | |
| O=CN (morpholinyl) | H | CH₃ | OCH₂CH₃ | OCH₃ | N | |
| O=CN (pyrrolidinyl) | H | CH₃ | OCH₃ | N(CH₃)₂ | N | |
| O=CN(CH₂CH₂CH₃)₂ | H | CH₃ | CH₃ | CH(OCH₃)₂ | CH | |
| O=CCH₃ | 6-Cl | CH₃ | OCH₃ | OCH₃ | CH | |
| O=CCH₃ | 6-Cl | CH₃ | OCH₃ | N(CH₃)₂ | CH | |
| O=CCH₂CH₃ | 5-Cl | CH₃ | CH₃ | OCH₃ | CH | |
| O=CCH₂CH₂CH₃ | 5-Cl | CH₃ | CH₃ | CH₃ | CH | |
| O=CCF₃ | 4-Cl | CH₃ | CH₃ | N(CH₃)₂ | CH | |
| O=CPh | 4-Cl | CH₃ | CH₃ | CH₃ | N | |
| O=COCH₃ | 3-Cl | C₂H₅ | OCH₃ | CH₃ | N | |
| O=COCH₂CH₃ | 3-Cl | CH₃ | OCH₃ | OCH₃ | N | |
| O=CCH₃ | 6-Br | CH₃ | CH₃ | C₂H₅ | N | |
| O=CO(CH₂)₃CH₃ | 6-Br | CH₃ | OCH₃ | C₂H₅ | N | |

TABLE VIa-continued

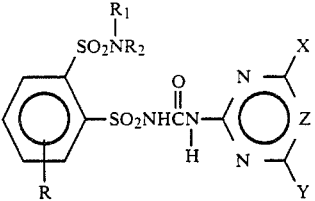

| R₁ | R | R₂ | X | Y | Z | m.p. (°C.) |
|---|---|---|---|---|---|---|
| $\underset{CNH_2}{\overset{O}{\|}}$ | 5-Br | CH₃ | CH₃ | OC₂H₅ | N | |
| $\underset{CNHCH_3}{\overset{O}{\|}}$ | 5-Br | CH₃ | OCH₃ | OC₂H₅ | N | |
| $\underset{CNH_2}{\overset{O}{\|}}$ | 4-Br | CH₃ | CH₃ | CH₂OCH₃ | N | |
| $\underset{CNHCH_2CH_3}{\overset{O}{\|}}$ | 3-Br | CH₃ | OCH₃ | CH₂OCH₃ | N | |
| $\underset{CNH(CH_2)_3CH_3}{\overset{O}{\|}}$ | 6-F | CH₃ | OCH₃ | OCH₃ | N | |
| $\underset{CNHPh}{\overset{O}{\|}}$ | 5-F | CH₃ | OCH₃ | CH₃ | N | |
| $\underset{CN(CH_3)_2}{\overset{O}{\|}}$ | 4-F | CH₃ | OCH₃ | N(CH₃)₂ | N | |
| $\underset{CN(CH_3)CH_2CH_3}{\overset{O}{\|}}$ | 3-F | CH₃ | CH₃ | 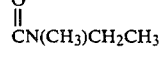 | CH | |
| $\underset{CN(CH_3)Ph}{\overset{O}{\|}}$ | 6-OCH₃ | CH₃ | OCH₃ | 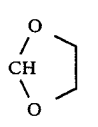 | CH | |
| $\underset{CN(CH_2CH_3)_2}{\overset{O}{\|}}$ | 5-OCH₃ | CH₃ | CH₃ | 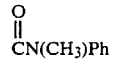 | N | |
| $\underset{CN(CH_2CH_3)Ph}{\overset{O}{\|}}$ | 5-OCH₃ | CH₃ | OCH₃ | 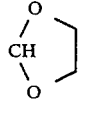 | N | |
| 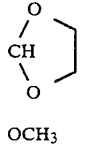 | 4-OCH₃ | CH₃ | Cl | OCH₃ | CH | |
| 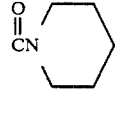 | 3-OCH₃ | CH₃ | CH₃ | CH₃ | CH | |
|  | 6-CF₃ | CH₃ | OCH₃ | CH₃ | CH | |

TABLE VIa-continued

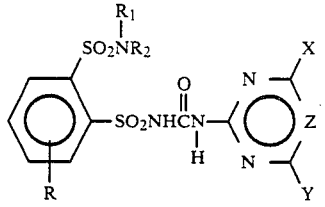

| $R_1$ | R | $R_2$ | X | Y | Z | m.p. (°C.) |
|---|---|---|---|---|---|---|
| $\overset{O}{\underset{}{\|}}$ CCH$_3$ | 5-CF$_3$ | CH$_3$ | OCH$_3$ | OCH$_3$ | CH | |
| $\overset{O}{\underset{}{\|}}$ CCH$_2$CH$_3$ | 4-CF$_3$ | CH$_3$ | CH$_3$ | C$_2$H$_5$ | CH | |
| $\overset{O}{\underset{}{\|}}$ COCH$_3$ | 4-CF$_3$ | CH$_3$ | OCH$_3$ | C$_2$H$_5$ | CH | |
| $\overset{O}{\underset{}{\|}}$ CNH$_2$ | 3-CF$_3$ | CH$_3$ | CH$_3$ | OC$_2$H$_5$ | CH | |
| $\overset{O}{\underset{}{\|}}$ CCH$_3$ | H | n-C$_3$H$_7$ | CH$_3$ | CH$_2$F | CH | |
| $\overset{O}{\underset{}{\|}}$ CCH$_3$ | H | CH$_3$ | OCH$_3$ | CH$_2$F | CH | |
| $\overset{O}{\underset{}{\|}}$ CCH$_3$ | H | CH$_3$ | CH$_3$ | CH$_2$F | N | |
| $\overset{O}{\underset{}{\|}}$ CCH$_3$ | H | CH$_3$ | OCH$_3$ | CH$_2$F | N | |

TABLE VIb

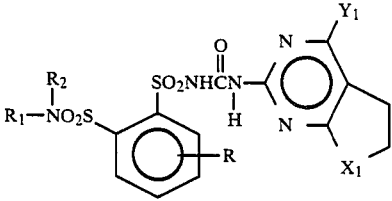

| R | $R_1$ | $R_2$ | $X_1$ | $Y_1$ | m.p. (°C.) |
|---|---|---|---|---|---|
| H | $\overset{O}{\underset{}{\|}}$ CCH$_3$ | CH$_3$ | O | CH$_3$ | |
| H | $\overset{O}{\underset{}{\|}}$ CCF$_3$ | CH$_3$ | O | OCH$_3$ | |
| H | $\overset{O}{\underset{}{\|}}$ COCH$_3$ | CH$_3$ | CH$_2$ | CH$_3$ | |
| H | $\overset{O}{\underset{}{\|}}$ CN(piperidine) | CH$_3$ | CH$_2$ | OCH$_3$ | |
| H | $\overset{O}{\underset{}{\|}}$ CCH$_3$ | C$_2$H$_5$ | O | Cl | |

TABLE VIb-continued

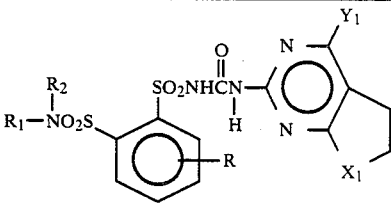

| R | $R_1$ | $R_2$ | $X_1$ | $Y_1$ | m.p. (°C.) |
|---|---|---|---|---|---|
| 5-Cl | $\overset{O}{\underset{}{\|}}$ CCF$_3$ | CH$_3$ | O | CH$_3$ | |
| 3-Cl | $\overset{O}{\underset{}{\|}}$ CNH$_2$ | CH$_3$ | CH$_2$ | OCH$_3$ | |
| 5-CF$_3$ | $\overset{O}{\underset{}{\|}}$ CN(CH$_3$)$_2$ | CH$_3$ | CH$_2$ | CH$_3$ | |
| 4-CF$_3$ | $\overset{O}{\underset{}{\|}}$ COCH$_2$CH$_3$ | CH$_3$ | O | CH$_3$ | |
| 6-Br | $\overset{O}{\underset{}{\|}}$ CNHCH$_2$CH$_3$ | CH$_3$ | CH$_2$ | OCH$_3$ | |

TABLE VIb-continued

Structure: R₂-N(R₁)-SO₂-phenyl(R)-SO₂NHC(O)NH-pyrimidine with X₁, Y₁ substituents

| R | R₁ | R₂ | X₁ | Y₁ | m.p. (°C.) |
|---|---|---|---|---|---|
| 4-F | C(O)N-morpholino | CH₃ | O | H | |
| H | COCH₂CH₃ | i-C₃H₇ | O | H | |
| 5-OCH₃ | CNH₂(O) | CH₃ | O | OCH₃ | |
| H | CF₂H | CH₃ | O | CH₃ | |
| H | CF₂H | CH₃ | CH | OCH₃ | |

TABLE VIc

Structure: R₁-N(R₂)-SO₂-phenyl(R)-SO₂NHC(O)NH-triazole with X₂, Y₂ substituents

| R | R₁ | R₂ | Y₂ | X₂ |
|---|---|---|---|---|
| H | COCH₃ | CH₃ | CH₃ | SCH₃ |
| H | CCF₃(O) | CH₃ | CH₂CF₃ | SCH₃ |
| H | COCH₃ | CH₃ | CH₃ | OCH₃ |
| H | COCH₃ | CH₃ | C₂H₅ | SCH₃ |
| H | CCF₃(O) | n-C₃H₇ | C₂H₅ | CH₃ |
| H | CNH₂(O) | CH₃ | C₂H₅ | OCH₃ |
| H | CN(CH₃)₂(O) | CH₃ | CH₃ | CH₃ |
| H | CNHCH₂CH₃(O) | CH₃ | CH₂CF₃ | OCH₃ |
| 6-Cl | COCH₃ | CH₃ | CH₃ | OCH₃ |
| 5-Cl | COCH₃ | CH₃ | CH₃ | OCH₃ |

TABLE VIc-continued

| R | R₁ | R₂ | Y₂ | X₂ |
|---|---|---|---|---|
| 4-Cl | CCF₃(O) | C₂H₅ | CH₃ | OCH₃ |
| 5-Br | COCH₃ | CH₃ | CH₃ | OCH₃ |
| 4-Br | CNH₂(O) | CH₃ | CH₃ | OCH₃ |
| 4-F | CCF₃(O) | CH₃ | CH₃ | OCH₃ |
| 3-F | CCH₃(O) | CH₃ | CH₃ | OCH₃ |
| 6-OCH₃ | COCH₂CH₃ | CH₃ | CH₃ | OCH₃ |
| 5-OCH₃ | CN(CH₃)₂(O) | CH₃ | CH₃ | OCH₃ |
| 4-OCH₃ | CCH₃(O) | CH₃ | CH₃ | OCH₃ |
| 6-CF₃ | CCF₃(O) | CH₃ | CH₃ | OCH₃ |
| 5-CF₃ | COCH₂CH₃ | CH₃ | CH₃ | OCH₃ |
| H | CF₂H | CH₃ | CH₃ | OCH₃ |
| H | CF₂H | CH₃ | CH₃ | CH₃ |

TABLE VId

Structure: R₁-N(R₂)-SO₂-phenyl(R)-SO₂NHC(O)NH-pyrimidine with Y₁, Y₃ substituents (furo-fused)

| R | R₁ | R₂ | Y₁ | Y₃ | m.p. (°C.) |
|---|---|---|---|---|---|
| H | COCH₃ | CH₃ | CH₃ | H | |
| H | COCH₂CH₃ | CH₃ | OCH₃ | CH₃ | |
| H | CCF₃(O) | CH₃ | Cl | CH₃ | |

TABLE VId-continued

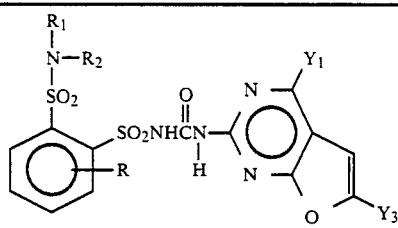

| R | R₁ | R₂ | Y₁ | Y₃ | m.p. (°C.) |
|---|---|---|---|---|---|
| 5-Cl | $\underset{CNH_2}{\overset{O}{\|\|}}$ | CH₃ | OCH₃ | CH₃ | |
| 4-Cl | $\underset{CNHCH_3}{\overset{O}{\|\|}}$ | CH₃ | CH₃ | CH₃ | |
| 5-Br | $\underset{CNHCH_2CH_3}{\overset{O}{\|\|}}$ | CH₃ | OCH₃ | CH₃ | |
| 4-Br | pyrrolidinyl-C(O)- | | CH₃ | CH₃ | CH₃ |
| 4-F | $\underset{CCH_3}{\overset{O}{\|\|}}$ | i-C₃H₇ | OCH₃ | H | |
| 3-F | $\underset{CCF_3}{\overset{O}{\|\|}}$ | C₂H₅ | CH₃ | CH₃ | |
| H | $\underset{COCH_3}{\overset{O}{\|\|}}$ | CH₃ | H | H | |
| 5-OCH₃ | morpholinyl-C(O)- | | CH₃ | CH₃ | CH₃ |
| 4-OCH₃ | $\underset{COCH_3}{\overset{O}{\|\|}}$ | CH₃ | OCH₃ | CH₃ | |
| 6-CF₃ | $\underset{CCH_3}{\overset{O}{\|\|}}$ | CH₃ | CH₃ | -CH₃ | |
| 5-CF₃ | $\underset{CCF_3}{\overset{O}{\|\|}}$ | CH₃ | OCH₃ | CH₃ | |
| H | CF₂H | CH₃ | OCH₃ | H | |

TABLE VIe

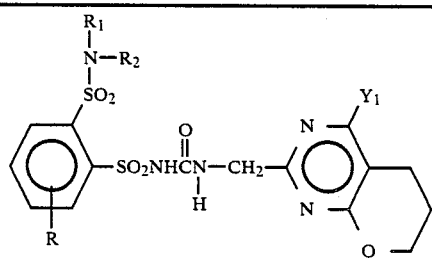

| R | R₁ | R₂ | Y | m.p. (°C.) |
|---|---|---|---|---|
| H | $\underset{CCH_3}{\overset{O}{\|\|}}$ | CH₃ | CH₃ | |

TABLE VIe-continued

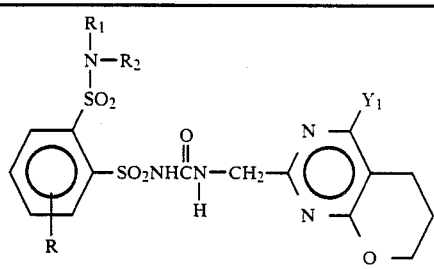

| R | R₁ | R₂ | Y | m.p. (°C.) |
|---|---|---|---|---|
| H | $\underset{CCH_3}{\overset{O}{\|\|}}$ | CH₃ | Cl | |
| H | $\underset{CCH_3}{\overset{O}{\|\|}}$ | CH₃ | OCH₃ | |
| H | $\underset{COCH_2CH_3}{\overset{O}{\|\|}}$ | CH₃ | H | |
| H | $\underset{CNH_2}{\overset{O}{\|\|}}$ | CH₃ | OCH₃ | |
| 6-Cl | $\underset{CCH_3}{\overset{O}{\|\|}}$ | n-C₃H₇ | CH₃ | |
| 5-Br | $\underset{CCH_3}{\overset{O}{\|\|}}$ | CH₃ | OCH₃ | |
| 4-F | $\underset{CCH_3}{\overset{O}{\|\|}}$ | CH₃ | OCH₃ | |
| 3-CF₃ | $\underset{CCH_3}{\overset{O}{\|\|}}$ | CH₃ | OCH₃ | |
| 6-OCH₃ | $\underset{COCH_2CH_3}{\overset{O}{\|\|}}$ | CH₃ | OCH₃ | |
| H | CF₂H | CH₃ | OCH₃ | |

TABLE VIf

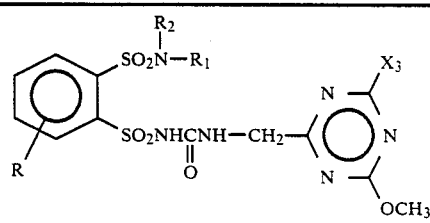

| R | R₁ | R₂ | X₃ | m.p. (°C.) |
|---|---|---|---|---|
| H | $\underset{CCH_3}{\overset{O}{\|\|}}$ | CH₃ | CH₃ | |
| H | $\underset{COCH_2CH_3}{\overset{O}{\|\|}}$ | CH₃ | OCH₃ | |
| 6-Cl | $\underset{CN(CH_3)_2}{\overset{O}{\|\|}}$ | CH₃ | OCH₃ | |

TABLE VIf-continued

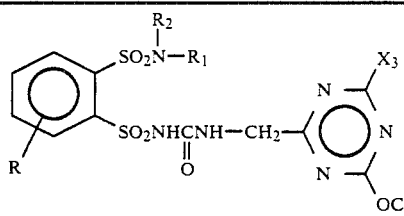

| R | R₁ | R₂ | X₃ | m.p. (°C.) |
|---|----|----|----|-----------|
| 5-Br | $\underset{CNH_2}{\overset{O}{\|}}$ | CH₃ | OCH₃ | |
| 4-F | $\underset{CCF_3}{\overset{O}{\|}}$ | C₂H₅ | OCH₃ | |
| H | CF₂H | CH₃ | CH₃ | |

TABLE VII

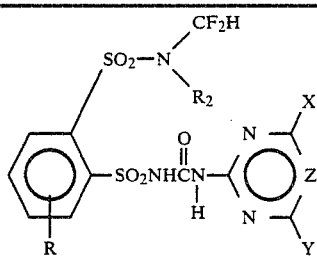

| R | R₂ | X | Y | Z | m.p. (°C.) |
|---|----|----|----|----|-----------|
| H | CH₃ | CH₃ | CH₃ | CH | 210–215° C. (dec) |
| H | CH₃ | OCH₃ | CH₃ | CH | 210–211° C. |
| H | CH₃ | OCH₃ | OCH₃ | CH | 201–203° C. |
| H | CH₃ | CH₃ | C₂H₅ | CH | |
| H | CH₃ | OCH₃ | C₂H₅ | CH | |
| H | CH₃ | CH₃ | OC₂H₅ | CH | |
| H | CH₃ | OCH₃ | OC₂H₅ | CH | |
| H | CH₃ | CH₃ | CH₂OCH₃ | CH | |
| H | CH₃ | OCH₃ | CH₂OCH₃ | CH | |
| H | CH₃ | Br | OC₂H₅ | CH | |
| H | CH₃ | Br | OCH₃ | CH | |
| H | CH₃ | OCH₃ | N(CH₃)₂ | CH | |
| H | CH₃ | CH₃ | CH₃ | N | |
| H | CH₃ | OCH₃ | CH₃ | N | 185–186° C. |
| H | CH₃ | OCH₃ | OCH₃ | N | 179–181° C. |
| H | CH₃ | CH₃ | C₂H₅ | N | |
| H | CH₃ | OCH₃ | C₂H₅ | N | |
| H | CH₃ | CH₃ | OC₂H₅ | N | |
| H | CH₃ | OCH₃ | OC₂H₅ | N | |
| H | CH₃ | CH₃ | CH₂OCH₃ | N | |
| H | CH₃ | OCH₃ | CH₂OCH₃ | N | |
| H | CH₃ | OCF₂H | OCH₃ | N | |
| H | CH₃ | OCH₂CH₃ | OCH₃ | N | |
| H | CH₃ | OCH₃ | N(CH₃)₂ | N | |
| H | CH₃ | CH₃ | CH(OCH₃)₂ | CH | |
| H | CH₃ | OCH₃ | CH(OCH₃)₂ | CH | |
| H | C₂H₅ | CH₃ | CH₃ | CH | |
| H | C₂H₅ | OCH₃ | CH₃ | CH | |
| H | C₂H₅ | OCH₃ | OCH₃ | CH | |
| H | C₂H₅ | CH₃ | C₂H₅ | CH | |
| H | C₂H₅ | OCH₃ | C₂H₅ | CH | |
| H | C₂H₅ | CH₃ | OC₂H₅ | CH | |
| H | C₂H₅ | OCH₃ | OC₂H₅ | CH | |
| H | C₂H₅ | OCH₃ | CH₃ | N | |
| H | C₂H₅ | CH₃ | CH₃ | N | |
| H | C₂H₅ | OCH₃ | OCH₃ | N | |
| H | C₂H₅ | Br | OC₂H₅ | CH | |
| H | C₂H₅ | Br | OCH₃ | CH | |
| H | C₂H₅ | OCH₃ | N(CH₃)₂ | CH | |
| H | n-C₃H₇ | CH₃ | CH₃ | N | |
| H | n-C₃H₇ | OCH₃ | CH₃ | N | |
| H | n-C₃H₇ | OCH₃ | OCH₃ | N | |
| H | n-C₃H₇ | CH₃ | C₂H₅ | N | |

TABLE VII-continued

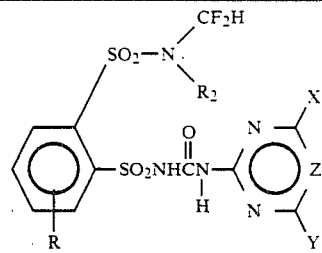

| R | R₂ | X | Y | Z | m.p. (°C.) |
|---|----|----|----|----|-----------|
| H | n-C₃H₇ | OCH₃ | C₂H₅ | N | |
| H | n-C₃H₇ | CH₃ | OC₂H₅ | N | |
| H | n-C₃H₇ | OCH₃ | CH₃ | CH | |
| H | n-C₃H₇ | CH₃ | CH₃ | CH | |
| H | n-C₃H₇ | OCH₃ | OCH₃ | CH | |
| H | n-C₃H₇ | OCF₂H | OCH₃ | N | |
| H | n-C₃H₇ | OCH₂CH₃ | OCH₃ | N | |
| H | n-C₃H₇ | OCH₃ | N(CH₃)₂ | N | |
| H | n-C₃H₇ | CH₃ | CH(OCH₃)₂ | CH | |
| H | n-C₃H₇ | OCH₃ | CH(OCH₃)₂ | CH | |
| H | CH₃ | CH₃ | 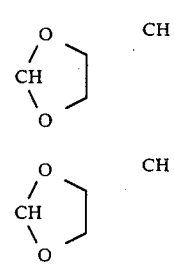 | CH | |
| H | CH₃ | OCH₃ |  | CH | |
| H | CH₃ | CH₃ | CH(OCH₃)₂ | N | |
| H | CH₃ | OCH₃ | CH(OCH₃)₂ | N | |
| H | CH₃ | CH₃ |  | N | |
| H | CH₃ | OCH₃ | (same) | N | |
| H | CH₃ | Cl | OCH₃ | CH | |
| H | CH₃ | Cl | OC₂H₅ | CH | |
| H | CH₃ | Cl | NHCH₃ | CH | |
| H | CH₃ | Cl | N(CH₃)₂ | CH | |
| H | CH₃ | CH₃ | SCH₃ | N | |
| H | CH₃ | OCH₃ | SCH₃ | N | |
| H | CH₃ | CH₃ | SCH₃ | CH | |
| H | CH₃ | OCH₃ | SCH₃ | CH | |
| 6-Cl | CH₃ | OCH₃ | OCH₃ | CH | |
| 6-Cl | CH₃ | OCH₃ | N(CH₃)₂ | CH | |
| 5-Cl | CH₃ | CH₃ | OCH₃ | CH | |
| 5-Cl | CH₃ | CH₃ | CH₃ | CH | |
| 4-Cl | CH₃ | CH₃ | N(CH₃)₂ | CH | |
| 4-Cl | CH₃ | CH₃ | CH₃ | N | |
| 3-Cl | CH₃ | OCH₃ | CH₃ | N | |
| 3-Cl | CH₃ | OCH₃ | OCH₃ | N | |
| 6-Br | CH₃ | CH₃ | C₂H₅ | N | |
| 6-Br | CH₃ | OCH₃ | C₂H₅ | N | |
| 5-Br | CH₃ | CH₃ | OC₂H₅ | N | |
| 5-Br | CH₃ | OCH₃ | OC₂H₅ | N | |
| 4-Br | CH₃ | CH₃ | CH₂OCH₃ | N | |
| 3-Br | CH₃ | OCH₃ | CH₂OCH₃ | N | |
| 6-F | CH₃ | OCH₃ | OCH₃ | N | |
| 5-F | CH₃ | CH₃ | CH₃ | N | |
| 4-F | CH₃ | OCH₃ | N(CH₃)₂ | N | |

TABLE VII-continued $$\begin{array}{c}\text{structure with } SO_2-N(CF_2H)(R_2), \text{ benzene ring with } R, \\ SO_2NHC(=O)N-H, \text{ pyrimidine ring with } X, Y, Z\end{array}$$

| R | R₂ | X | Y | Z | m.p. (°C.) |
|---|----|----|----|----|-----------|
| 3-F | CH₃ | CH₃ | O-CH₂-O | CH | |
| 6-OCH | CH₃ | OCH₃ | O-CH₂-O | CH | |
| 5-OCH₃ | CH₃ | OCH₃ | O-CH₂-O | N | |
| 5-OCH₃ | CH₃ | OCH₃ | O-CH₂-O | N | |
| 4-OCH₃ | CH₃ | Cl | OCH₃ | CH | |
| 3-OCH₃ | CH₃ | CH₃ | CH₃ | CH | |
| 6-CF₃ | CH₃ | OCH₃ | CH₃ | CH | |
| 5-CF₃ | CH₃ | OCH₃ | OCH₃ | CH | |
| 4-CF₃ | CH₃ | CH₃ | C₂H₅ | CH | |
| 4-CF₃ | CH₃ | OCH₃ | C₂H₅ | CH | |
| 3-CF₃ | CH₃ | CH₃ | OC₂H₅ | CH | |
| H | CH₃ | CH₃ | CH₂F | CH | |
| H | CH₃ | OCH₃ | CH₂F | CH | |
| H | CH₃ | CH₃ | CH₂F | N | |
| H | CH₃ | OCH₃ | CH₂F | N | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VIII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either minced or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8-57ff.

EXAMPLE 10

Wettable Powder
  N-[(4,6-Dimethoxypyrimidin-2-yl)aminocarbonyl]-1,2-benzenedisulfonamide: 80%
  sodium alkylnaphthalenesulfonate: 2%
  sodium ligninsulfonate: 2%
  synthetic amorphous silica: 3%
  kaolinite: 13%

The ingredients are blended, hammer-milled until all the solids are essentially under 50 microns, reblended, and packaged.

EXAMPLE 11

Wettable Powder
  N-[(4-Methoxy-6-methylpyrimidin-2-yl)aminocarbonyl]-1,2-benzenedisulfonamide: 50%
  sodium alkylnaphthalenesulfonate: 2%
  low viscosity methyl cellulose: 2%
  diatomaceous earth: 46%

The ingredients are blended, coarsely hammer-milled and then air-milled to produce particles essentially all below 10 microns in diameter. The product is reblended before packaging.

EXAMPLE 12

Granule
  Wettable Powder of Example 11: 5%
  attapulgite granules (U.S.S. 20–40 mesh; 0.84–0.42 mm): 95%

A slurry of wettable powder containing 25% solids is sprayed on the surface of attapulgite granules in a double-cone blender. The granules are dried and packaged.

EXAMPLE 13

Extruded Pellet
  2-(Azetidin-1-ylsulfonyl)-N-[(4,6-dimethoxy-1,3,5-triazin-2-yl)aminocarbonyl]benzenesulfonamide: 25%
  anhydrous sodium sulfate: 10%
  crude calcium ligninsulfonate: 5%
  sodium alkylnaphthalenesulfonate: 1%
  calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

Low Strength Granule
  N,N'-bis[4,6-Dimethoxypyrimidin-2-yl)aminocarbonyl]-1,2-benzenedisulfonamide: 0.1%
  attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 15

Granule
  2-(Azetidin-1-ylsulfonyl)-N-[(4-methoxy-6-methylpyrimidin-2-yl)aminocarbonyl]benzenesulfonamide: 80%
  wetting agent: 1%
  crude ligninsulfonate salt (containing 5–20% of the natural sugars): 10%
  attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 16

Low Strength Granule
  N-[(4,6-Dimethoxypyrimidin-2-yl)aminocarbonyl]-1,2-benzenedisulfonamide: 1%
  N,N-dimethylformamide 9%
  attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 17

Aqueous Suspension
  N-[(4-Methoxy-6-methylpyrimidin-2-yl)aminocarbonyl]-1,2-benzenedisulfonamide: 40%
  polyacrylic acid thickener: 0.3%
  dodecylphenol polyethylene glycol ether: 0.5%
  disodium phosphate: 1%
  monosodium phosphate: 0.5%
  polyvinyl alcohol: 1.0%
  water:

The ingredients are blended and ground together in a sand mill to produce particles essentially all under 5 microns in size.

Example 18

Solution
  2-(Azetidin-1-ylsulfonyl)-N-[(4,6-dimethoxy-1,3,5-triazin-2-yl)aminocarbonyl]benzenesulfonamide, sodium salt: 5%
  water: 95%

The salt is added directly to the water with stirring to produce the solution, which may then be packaged for use.

EXAMPLE 19

High Strength Concentrate
  N,N'-Bis[(4,6-dimethoxypyrimidin-2-yl)aminocarbonyl]-1,2-benzenedisulfonamide: 99%
  silica aerogel: 0.5%
  synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 20

Wettable Powder
  2-(Azetidin-1-sulfonyl)-N-[(4-methoxy-6-methylpyrimidin-2-yl)aminocarbonyl]benzenesulfonamide: 90%
  dioctyl sodium sulfosuccinate: 0.1%
  synthetic fine silica: 9.9%

The ingredients are blended and ground in a hammer-mill to produce particles essentially all below 100 microns. The material is sifted through a U.S.S. No. 50 screen and then packaged.

EXAMPLE 21

Wettable Powder
  N-[(4,6-Dimethoxypyrimidin-2-yl)aminocarbonyl]-1,2-benzenedisulfonamide: 40%
  sodium ligninsulfonate: 20%
  montmorillonite clay: 40%

The ingredients are thoroughly blended, coarsely hammer-milled and then air-milled to produce particles essentially all below 10 microns in size. The material is reblended and then packaged.

EXAMPLE 22

Oil Suspension
  N-[(4-Methoxy-6-methylpyrimidin-2-yl)aminocarbonyl]-1,2-benzenedisulfonamide: 35%
  blend of polyalcohol carboxylic esters and oil soluble petroleum sulfonates: 6%
  xylene: 59%

The ingredients are combined and ground together in a sand mill to produce particles essentially all below 5 microns. The product can be used directly, extended with oils, or emulsified in water.

Example 23

Dust
  2-(Azetidin-1-ylsulfonyl)-N-[(4,6-dimethoxy-1,3,5-triazin-2-yl)aminocarbonyl]benzenesulfonamide: 10%
  attapulgite: 10%
  Pyrophyllite: 80%

The active ingredient is blended with attapulgite and then passed through a hammer-mill to produce particles substantially all below 200 microns. The ground concentrate is then blended with powdered pyrophyllite until homogeneous.

EXAMPLE 24

Oil Suspension
  N,N'-bis[(4,6-Dimethoxypyrimidin-2-yl)aminocarbonyl]-1,2-benzenedisulfonamide: 25%
  polyoxyethylene sorbitol hexaoleate: 5%
  highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 25

Wettable Powder
  N-[(4,6-Dimethoxypyrimidin-2-yl)aminocarbonyl]-1,2-benzenedisulfonamide: 20%
  sodium alkylnaphthalenesulfonate: 4%
  sodium ligninsulfonate: 4%
  low viscosity methyl cellulose: 3%
  attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

Utility

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.01 to 10 kg/ha, the lower rates being suggested for use on lighter soils and/or those having a low organic matter content, or for situations where only short-term persistence is required.

The compounds of the invention may be used in combination with any other commercial herbicide; examples of which are those of the triazine, triazole, uracil, urea, amide, diphenylether, carbamate, and bipyridylium types.

The herbicidal properties of the subject compounds were discovered in a number of greenhouse tests. The test procedures and results follow.

COMPOUNDS

Compound 1: phenyl-R, R is $-SO_2NHCNH-$ (C=O), pyrimidinyl with 4-CH$_3$, 6-CH$_3$ Compound 2: phenyl-R, R is $-SO_2NHCNH-$ (C=O), pyrimidinyl with 4-CH$_3$, 6-OCH$_3$ Compound 3: phenyl-R, R is $-SO_2NHCNH-$ (C=O), pyrimidinyl with 4-OCH$_3$, 6-OCH$_3$ Compound 4: phenyl-R, R is $-SO_2NHCNH-$ (C=O), triazinyl with 4-CH$_3$, 6-CH$_3$ Compound 5: phenyl-R, R is $-SO_2NHCNH-$ (C=O), triazinyl with 4-CH$_3$, 6-OCH$_3$ Compound 6: phenyl-R, R is $-SO_2NHCNH-$ (C=O), triazinyl with 4-OCH$_3$, 6-OCH$_3$

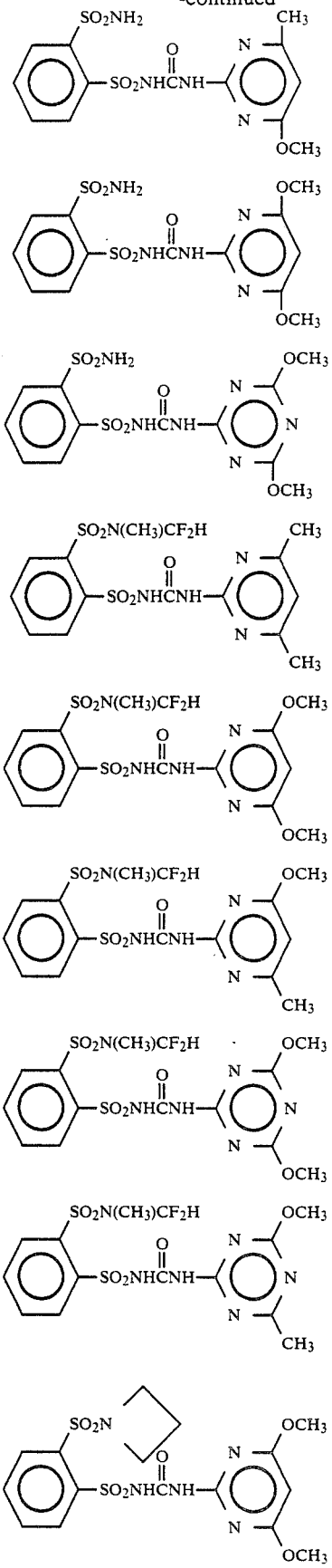
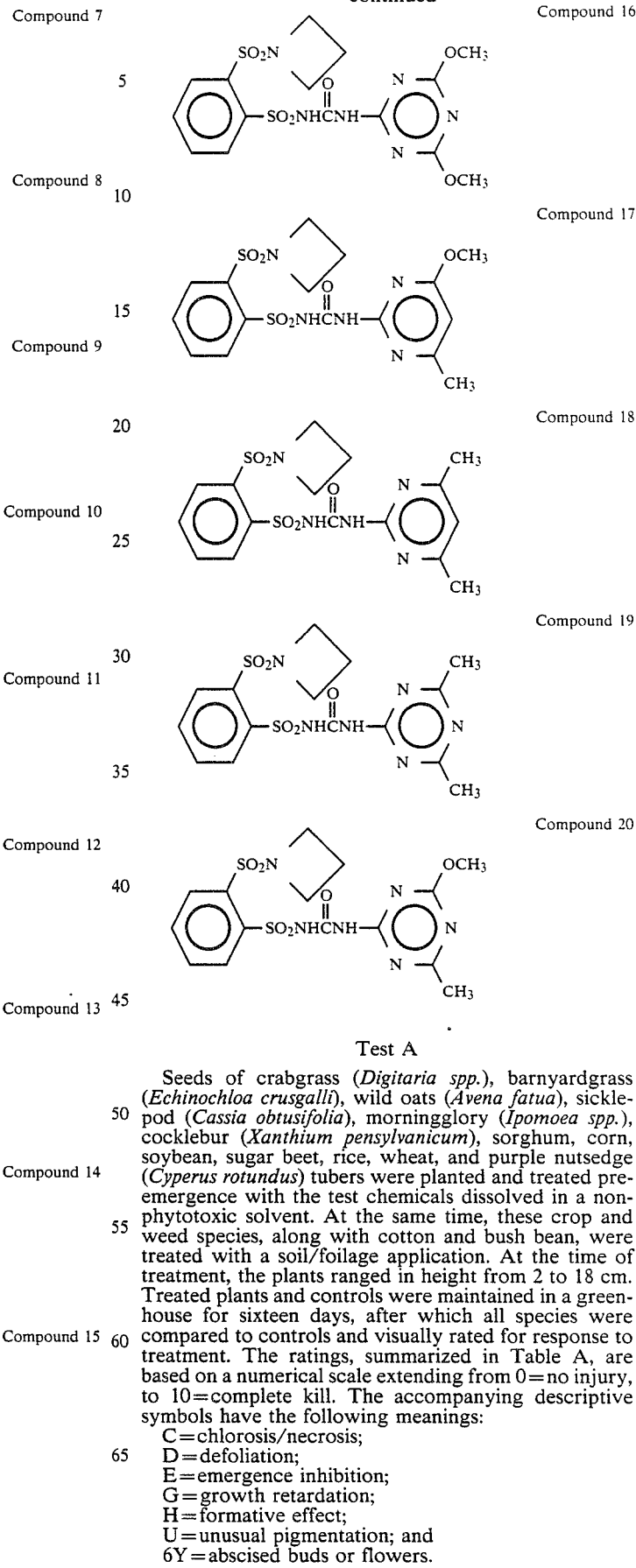

Test A

Seeds of crabgrass (*Digitaria spp.*), barnyardgrass (*Echinochloa crusgalli*), wild oats (*Avena fatua*), sicklepod (*Cassia obtusifolia*), morningglory (*Ipomoea spp.*), cocklebur (*Xanthium pensylvanicum*), sorghum, corn, soybean, sugar beet, rice, wheat, and purple nutsedge (*Cyperus rotundus*) tubers were planted and treated preemergence with the test chemicals dissolved in a non-phytotoxic solvent. At the same time, these crop and weed species, along with cotton and bush bean, were treated with a soil/foilage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effect;
U=unusual pigmentation; and
6Y=abscised buds or flowers.

TABLE A

| Rate g/ha | Cmpd. 1 400 | Cmpd. 2 400 | Cmpd. 3 400 | Cmpd. 4 400 | Cmpd. 5 400 | Cmpd. 6 400 | Compound 7 50 | Compound 7 400 | Cmpd. 8 50 | Compound 9 50 | Compound 9 400 | Cmpd. 10 50 | Cmpd. 11 50 | Cmpd. 12 50 |
|---|---|---|---|---|---|---|---|---|---|---|---|---|---|---|
| POST-EMERGENCE | | | | | | | | | | | | | | |
| Bush bean | 4C,9G,6Y | 4C,9G,6Y | 3G | 3C,4H | 8D,9G,6Y | 2C,3H | 3C,5G,6Y | 3C,7G,6Y | 5D,9G,6Y | 0 | 5C,8H,6Y | — | — | — |
| Cotton | 4C,9G | 5C,9G | 3C,7G | 0 | 4C,8G | 3C,7G | 4C,9G | 4C,9G | 4C,9G | 0 | 4C,8G | 5C,9G | 5C,9G | 5C,9G |
| Morningglory | 3C,6G | 9C | 5C,9G | 0 | 3C,7G | 5C,8H | 3C,8G | 9C | 5C,9G | 0 | 3C,8G | 5C,9G | 9C | 5C,9G |
| Cocklebur | 3C,9G | 5C,9G | 5C,9G | 1C,2H | 3C,6H | 2C,4G | 5C,9G | 9C | 9C | 0 | 8G | 5C,9G | 9C | 5C,9G |
| Sicklepod | 3C,8H | 9C | 5C,9G | 1C | 3C,6H | 3C,6G | 5C,9G | 9C | 5C,9G | 0 | 3C,9G | 5C,9G | 9C | 6C,9G |
| Nutsedge | 5G | 9C | 2C,9G | 0 | 2G | 6G | 2C,9G | 9C | 9C | 4G | 3G | 3C,8G | 9G | 3C,8G |
| Crabgrass | 3C,8G | 9C | 9C | 1C,2H | 4C,9H | 3C,9H | 9G | 9C | 5C,9G | 2C,6H | 4C,9H | 3G | 2C,8G | 3C,8G |
| Barnyardgrass | 3C,9H | 9C | 9C | 2C,6H | 9C | 9C | 3C,9H | 9C | 9C | 2C | 9C | 4C,9H | 5C,9H | 4C,9G |
| Wild Oats | 2C,9G | 3C,9G | 3C,9G | 0 | 4C,9G | 9C | 2C,8G | 5C,9G | 9C | 2C | 5C,9G | 9C | 9C | 2C,9G |
| Wheat | 2C,8G | 9C | 4U,9G | 1C,5G | 9C | 9C | 2C,5G | 5C,9G | 5C,9G | 2C,9G | 6C,9G | 5G | 7G | 7G |
| Corn | 5C,9G | 3U,9H | 5U,9G | 1C,1H | 9C | 9C | 1U,9G | 3U,9G | 2C,8G | 2C,9G | 6C,9G | 2C,4G | 1U,9G | 3C,9H |
| Soybean | 4C,9G | 9C | 9C | 3C,9G | 4C,9G | 3C,8H | 4C,9G | 5C,9G | 7U,9G | 1H | 4C,9G | 3C,7G | 5C,9G | 5C,9G |
| Rice | 6C,9G | 6C,9G | 5C,9G | 3C,7G | 5C,9G | 5C,9G | 5C,9G | 6C,9G | 5C,9G | 4C,9H | 6C,9G | 5C,9G | 6C,9G | 5C,9G |
| Sorghum | 3C,9H | 4C,9G | 5C,9G | 3C,7G | 4C,9G | 5C,9G | 2C,9G | 3U,9G | 9C | 4C,9H | 4C,9G | 9G | 2U,9H | 4C,9H |
| Sugar beet | 9C | 9C | 9C | 2C,3H | 9C | 9C | 9C | 9C | 9C | 2C,1H | 9C | 9C | 9C | 9C |
| PRE-EMERGENCE | | | | | | | | | | | | | | |
| Morningglory | 8H | 9G | 9C | 0 | 0 | 3C,5H | 9G | 9C | 9C | 1C | 2C | 9G | 9G | 3C,9G |
| Cocklebur | 9H | 9H | 9H | — | 2C | 2H | 9H | — | 9H | 0 | 0 | 8H | 9H | 9H |
| Sicklepod | 8G | 5C,9G | 9G | 3G | 2C | 3C,8H | 2C,9G | 5C,9G | 9C | 2H | 2C | 2C,8G | 9C | 5C,9G |
| Nutsedge | 5G | 10E | 9G | 0 | 2C,5G | 0 | 3C,9H | 10E | 10E | 0 | 2G | 8G | 10E | 3C,9G |
| Crabgrass | 2G | 5C,9G | 8G | 2G | 5C,9H | 3G | 3C,9H | 5C,9H | 5C,9H | 2C,5H | 2G | 0 | 4G | 1C,3G |
| Barnyardgrass | 3C,7G | 9H | 9H | 2H | 4C,9H | 3C,9H | 2C,9G | 5C,9H | 2C,9H | 0 | 3C,9H | 2C,6G | 2C,9H | 3C,9H |
| Wild Oats | 2C,8G | 5C,9H | 3C,9G | 0 | 2C,9H | 2C,9G | 3C,9H | 6C,9H | 5C,9H | 2C,5H | 2C,9G | 3C,8H | 3C,9G | 4C,9G |
| Wheat | 2C,9G | 5C,9H | 2C,9G | 1C | 2C,9G | 3C,9G | 3C,9H | 10E | 2C,9G | 2H | 3C,9H | 2C,9H | 8G | 5C,9H |
| Corn | 9H | 10H | 9H | 0 | 3C,9H | 9H | 3C,8H | 10E | 10H | 2C,6G | 3C,9H | 2C,7H | 3C,9H | 6C,9H |
| Soybean | 2C,2H | 9H | 9H | 1C | 1C,1H | 1C | 10E | 9H | 9H | 2C | 2C | 10E | 9H | 9H |
| Rice | 10E | 10E | 10E | 0 | 10E | 10E | 9H | 10E | 9H | 2C,8G | 10E | 10E | 10E | 10E |
| Sorghum | 6C,9H | 5C,9H | 2C,9H | 2C | 10E | 5C,9H | 6C,9H | 5C,9H | 7C,9H | 4C,6G | 3C,9H | 7C,9H | 5C,9H | 5C,9H |
| Sugar beet | 5C,9G | 10E | 10E | 2H | 3C,8G | 2C,9H | 10E | 4C,9G | 9C | 0 | 6H | 5C,9G | 6C,9G | 6C,9G |
| Cotton | | | | | | | | | | | | 2C,9G | 2C,9G | 2C,9G |

| Rate g/ha | Cmpd. 13 50 | Cmpd. 14 50 | Cmpd. 15 50 | Cmpd. 16 50 | Cmpd. 17 50 | Cmpd. 18 50 | Cmpd. 19 50 | Cmpd. 20 50 |
|---|---|---|---|---|---|---|---|---|
| POST-EMERGENCE | | | | | | | | |
| Bush bean | 5C,9G | 4C,9H | 10C | — | — | 2C,9G | 3C,9H | 9C |
| Cotton | 6C,9G | 5C,9H | 5C,9G | 9C | 9C | 4C,9G | 4C,9G | 10C |
| Morningglory | 2C,9G | 5C,9G | 10C | 9C | 9C | 5C,9H | 4C,9H | 10C |
| Cocklebur | 6C,9G | 4C,7H | 6C,9G | 9C | 9C | 2C,3H | 1C | 4C,8G |
| Sicklepod | 3G | 2G | 9G | 5C,9G | 5C,9G | 4G | 2G | 3C,9G |
| Nutsedge | 5C,9G | 4C,7G | 6C,9G | 10C | 10C | 4G | 0 | 2C,5G |
| Crabgrass | 5C,9H | 4C,9H | 3C,9G | 5C,9G | 5C,9G | 4C,9H | 2C,7G | 3C,9H |
| Barnyardgrass | 8G | 2G | 9C | 9C | 2C,7G | 3C,8G | 0 | 2C,2H |
| Wild Oats | 5G | 2G | 10C | 1G | 9C | 9H | 0 | 2C,6G |
| Wheat | 3C,9G | 2U,9G | 3U,9G | 5C,9G | 5C,9G | 2C,9H | 3C,9H | 2C,6G |
| Corn | 9C | 4C,8H | 9C | 6C,9G | 6C,9G | 3C,9G | 3C,9H | 3C,9H |
| Soybean | 6C,9G | 5C,9G | 6C,9G | 9C | 9C | 5C,9G | 5C,9H | 6C,9G |
| Rice | 5C,9G | 5C,9G | 5U,9C | 2C,9H | 2C,9H | 5C,9G | 9G | 9C |
| Sorghum | 9C | 3C,9G | 5C,9G | 4C,9G | 4C,9G | 2C,9G | 1C,3G | 5C,9G |

TABLE A-continued

| | PRE-EMERGENCE | | | | | | |
|---|---|---|---|---|---|---|---|
| Morningglory | 9C | 9C | 9G | 9H | 9C | 8H | 9C |
| Cocklebur | 9H | 9H | 9H | 9H | 8H | 8H | 9C |
| Sicklepod | 9G | 6C,8H | 9G | 8G | 7G | 5G,2C | 4C,9G |
| Nutsedge | 4G | 2G | 10E | 10E | 5G | 0 | 8G |
| Crabgrass | 4C,9G | 1C | 3C,7G | 1C | 0 | 0 | 2C,5G |
| Barnyardgrass | 4C,9H | 3C,9H | 3C,9H | 4C,9H | 3C,8H | 5G | 3C,9H |
| Wild Oats | 4C,8G | 2C,8G | 2C,8G | 3C,9G | 3C,8G | 2C | 9G |
| Wheat | 5C,9G | 3G | 7C,9H | 10E | 8G | 0 | 2C,9G |
| Corn | 10E | 9G | 9H | 9H | 2C,8G | 9G | 3C,9G |
| Soybean | 4C,8H | 4C,6H | 9H | 9H | 7H | 3C,4H | 9H |
| Rice | 10E | 4C,9H | 10E | 10E | 10E | 9H | 10E |
| Sorghum | 6C,9H | 5C,9H | 4C,9H | 5C,9H | 3C,9H | 2C,9G | 5C,9H |
| Sugar Beet | 10E | 9C | 9G | 5C,9G | 8G | 5C,9G | 10E |
| Cotton | 5C,9G | 3C,8H | 3C,9G | 9G,3C | 8G | 8G | 3C,9G |

Test B

Two plastic bulb pans were filled with fertilized and limed Fallsington silt loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echincholoa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*) sicklepod (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON FALSINGTON SILT LOAM

| | Compound 2 | | | | | Compound 3 | | Compound 5 | | | | |
|---|---|---|---|---|---|---|---|---|---|---|---|---|
| Rate g/ha | 1 | 4 | 16 | 62 | 250 | 16 | 62 | 4 | 16 | 62 | 250 | 1000 |
| Crabgrass | 0 | 4G | 8G | 9G | 10C | 0 | 7G | 0 | 0 | 0 | 0 | 9G |
| Barnyardgrass | 0 | 4G | 7G | 9G | 9G | 0 | 8G | 0 | 0 | 0 | 2G | 9G |
| Sorghum | — | — | — | — | — | 3G | 9G | | | | | |
| Wild Oats | 0 | 2G | 5G | 8G | 9G | 0 | 2G | 0 | 0 | 0 | 0 | 9G |
| Johnsongrass | 3G | 7G | 9G | 9G | 10C | 2G | 8G | 3G | 0 | 0 | 6G | 10C |
| Dallisgrass | — | — | — | — | — | 2G | 8G | | | | | |
| Giant foxtail | 2G | 6G | 9G | 9G | 10C | 3G | 8G | 3G | 0 | 0 | 7G | 9G |
| Cheatgrass | — | — | — | — | — | 4G | 8G | | | | | |
| Sugar beets | 5G | 7G | 10C | 10C | 10C | 2G | 8G | 2G | 0 | 0 | 5G | 9G |
| Corn | 0 | 0 | 5G | 8G | 9G | 2G | 8G | 0 | 0 | 0 | 5G | 10C |
| Mustard | — | — | — | — | — | 9G | 9G | | | | | |
| Cocklebur | 0 | 0 | 5G | 8G | 9G | 0 | — | 0 | 0 | 0 | 0 | 7G |
| Nutsedge | 0 | 2G | 7G | 8G | 10C | 0 | 4G | 0 | 0 | 0 | 0 | 4C |
| Cotton | 0 | 3G | 5G | 9G | 9G | 2G | 2G | 0 | 0 | 0 | 3G | 5G |
| Morningglory | 0 | 0 | 4G | 9G | 9G | 0 | 0 | 0 | 0 | 0 | 0 | 7G |
| Sicklepod | 0 | 0 | 4G | 9G | 9G | 0 | 6G | 0 | 0 | 0 | 0 | 7G |
| Teaweed | 2G | 4G | 7G | 9G | 9G | 0 | 0 | 0 | 0 | 0 | 0 | 6G |
| Velvetleaf | 0 | 3G | 8G | 9G | 9G | 0 | 7G | 0 | 0 | 0 | 0 | 3G |
| Jimsonweed | 3G | 5G | 8G | 9G | 9G | 0 | 6G | 0 | 0 | 0 | 0 | 5G |
| Soybean | 0 | 0 | 6G | 9G | 9G | 0 | 3G | 0 | 0 | 0 | 2G | 5G |
| Rice | 7G | 9G | 9G | 10C | 10C | 8G | 10C | 0 | 0 | 0 | 9G | 9G |
| Wheat | 0 | 0 | 2G | 9G | 10C | 0 | 0 | 0 | 0 | 0 | 0 | 8G |
| Ky. bluegrass | | | | | | 0 | 9G | | | | | |

| | Compound 6 | | | | | Compound 7 | | Compound 8 | | Compound 9 | |
|---|---|---|---|---|---|---|---|---|---|---|---|
| Rate g/ha | 4 | 16 | 62 | 250 | 1000 | 2 | 16 | 4 | 31 | 31 | 250 |
| Crabgrass | 0 | 0 | 0 | 0 | 9G | 0 | 5G | 4G | 9G | 0 | 0 |
| Barnyardgrass | 0 | 0 | 0 | 0 | 8G | 0 | 4G | 8G | 9G | 0 | 0 |
| Sorghum | | | | | | 8G | 10C | 9G | 10C | 0 | 0 |
| Wild Oats | 0 | 0 | 0 | 0 | 7G | 0 | 3G | 2G | 9G | 0 | 0 |
| Johnsongrass | 0 | 0 | 0 | 0 | 9G | 0 | 8G | 7G | 10C | 0 | 0 |
| Dallisgrass | | | | | | 0 | 8G | 8G | 10C | 0 | 0 |
| Giant foxtail | 0 | 0 | 0 | 0 | 9G | 0 | 7G | 8G | 10C | 0 | 0 |
| Cheatgrass | | | | | | 7G | 9G | 9G | 10C | 0 | 3G |
| Sugar beets | 0 | 0 | 0 | 3G | 7G | 6G | 9G | 9G | 10C | 0 | 3G |
| Corn | 0 | 0 | 0 | 0 | 9G | 3G | 9G | 6G,5H | 9G | 0 | 5G |
| Mustard | | | | | | 3G | 9G | 9G | 9G | 0 | 3G |
| Cocklebur | 0 | 0 | 0 | 0 | 0 | 2G | 7G | 4G | 7G | 0 | 0 |
| Nutsedge | 0 | 0 | 0 | 0 | 9G | 3G | 9G | 2G | 10C | 0 | 0 |
| Cotton | 0 | 0 | 0 | 0 | 3G | 0 | 7G | 2G | 7G,5H | 0 | 0 |
| Morningglory | 0 | 0 | 0 | 0 | 0 | 0 | 5G | 0 | 4G | 0 | 0 |
| Sicklepod | 0 | 0 | 0 | 0 | 2G | 0 | 5G | 3G | 9G | 0 | 4G |
| Teaweed | 0 | 0 | 0 | 0 | 3G | 0 | 7G | 3G | 7G | 0 | 3G |
| Velvetleaf | 0 | 0 | 0 | 0 | 4G | 0 | 8G | 4G,4H | 9G | 0 | 5G |
| Jimsonweed | 0 | 0 | 0 | 0 | 3G | 0 | 9G | 7G | 9G | 0 | 3G |
| Soybean | 0 | 0 | 0 | 0 | 0 | 0 | 7G | 3G,3H | 9G | 0 | 0 |
| Rice | 0 | 0 | 6G | 9G | 9G | 7G | 10C | 10C | 10C | 0 | 9G |
| Wheat | 0 | 0 | 0 | 0 | 9G | 0 | 2G | 2G | 8G | 0 | 0 |
| Ky. bluegrass | | | | | | — | — | 5G | 9G | — | — |

Test C

The test chemical, dissolved in a non-phytotoxic solvent, was applied in an overall spray to the foliage and surrounding soil of selected plant species. One day after treatment, plants were checked for rapid burn injury. Approximately fourteen days after treatment all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, bush bean, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (*Digitaria spp.*), nutsedge (*Cyperus rotundus*), barnyardgrass (*Echinochloa crusgalli*), giant foxtail (*Setaria faberii*), and wild oats (*Avena fatua*). Sunflower and mustard were grown in soil in a paper cup (12 cm diameter by 13 cm deep). Additional plant species, such as johnsongrass and field bindweed are sometimes added to this standard test in order to evaluate unusual selectivity. All plants were sprayed approximately 14 days after planting.

The data show that the compound selected for this test possesses high post-emergence activity.

TABLE C

Over-the-Top Soil/Foliage Treatment

| | Compound 8 | |
|---|---|---|
| Rate g/ha | 16 | 62 |
| Soybeans | 10C | 10C |
| Velvetleaf | 7C,7G | 10C |
| Sesbania | 10C | 10C |
| Sicklepod | 9G | 10C |
| Cotton | 10C | 10C |
| Morningglory | 8G,7C | 8C,9G |
| Bush bean | 2G | 4G,3C |
| Jimsonweed | 10C | 9G |
| Cocklebur | — | 9G |
| Sunflower | 10C | 10C |
| Mustard | 5G | 7G |
| Corn | 8G,7C | 9C |
| Crabgrass | 9C | 9C |
| Rice | 8C,8G | 9G |
| Nutsedge | 7G | 8G |
| Barnyardgrass | 9C | 10C |
| Wheat | 4G | 7G |
| Giant foxtail | 9C | 10C |
| Wild Oats | 6G | 6C,7G |

TABLE C-continued

Over-the-Top Soil/Foliage Treatment

| | Compound 8 | |
|---|---|---|
| Rate g/ha | 16 | 62 |
| Sorghum | 9G,9C | 10C |
| Johnsongrass | 9C | 10C |
| Field Bindweed | 5G | 6G |

Test D

Postemergence

Two round pans (25 cm diameter by 12.5 cm deep) were filled with Sassafras sandy loam soil. One pan was planted with blackgrass, sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xantium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Pre-emergence

Two round pans (25 cm diameter by 12.5 cm deep) were filled with Sassafras sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described previously for Test A.

Response ratings are contained in Table D.

TABLE D

| | Compound 10 | | | Compound 11 | | | Compound 12 | | | Compound 13 | | | Compound 14 | | | Compound 15 | | | Compound 16 | | |
|---|---|---|---|---|---|---|---|---|---|---|---|---|---|---|---|---|---|---|---|---|---|
| Rate g/ha | 62 | 16 | 4 | 62 | 16 | 4 | 62 | 16 | 4 | 62 | 16 | 4 | 62 | 16 | 4 | 62 | 16 | 4 | 62 | 16 | 4 |
| | | | | | | | POST-EMERGENCE | | | | | | | | | | | | | | |
| Corn | 0 | 0 | 0 | 5G | 4G | 2G | 9G | 7G | 0 | 10C | 9G | 7G | 10G | 9G | 5G | 10C | 9G | 4G | 10C | 7G | 3G |
| Wheat | 0 | 0 | 0 | 5G | 2G | 0 | 5G | 4G | 0 | 0 | 0 | 0 | 2G | 0 | 0 | 10C | 10C | 3G | 0 | 0 | 0 |
| Rice | 10G | 9G | 6G | 10G | 8G | 3G | 10G | 10G | 7G | 10G | 9G | 5G | 10G | 9G | 5G | 10C | 10C | 10C | 10G | 5G | 10G |
| Soybean | 6G | 3G | 2G | 10G | 10G | 5G | 10G | 9G | 6G | 7G | 8G | 6G | 9G | 7G | 3G | 10C | 10C | 9G | 10G | 10G | 7G |
| Cotton | 9G | 6G | 0 | 9G | 8G | 0 | 10G | 9G | 5G | 8G | 6G | 4G | 8G | 8G | 3G | 10C | 6G | 4G | 10G | 8G | 5G |
| Sugar beet | 8G | 3G | 0 | 7G | 0 | 0 | 8G | 4G | 2G | 2G | 2G | 0 | 10G | 10G | 9G | 10C | 6G | 0 | 3G | 2G | 0 |
| Crabgrass | 4G | 0 | 0 | 4G | 0 | 0 | 5G | 0 | 0 | 0 | 0 | 0 | 9G | 5G | 0 | 3G | 3G | 0 | 10G | 5G | 0 |
| Johnsongrass | 9G | 7G | 4G | 7G | 2G | 2G | 9G | 6G | 3G | 10G | 8G | 4G | 10G | 10G | 9G | 10C | 7G | 4G | 9G | 9G | 7G |
| Blackgrass | 10G | 10G | 5G | 10G | 7G | 7G | 10G | 10G | 7G | 0 | 0 | 0 | 6G | 0 | 0 | 10C | 10C | 3G | 10G | 8G | 3G |
| Barnyardgrass | 8G | 5G | 3G | 7G | 2G | 0 | 7G | 7G | 2G | 8G | 10G | 4G | 10G | 6G | 0 | 10C | 10C | 5G | 10G | 5G | 0 |
| Nutsedge | 9G | 2G | 0 | 5G | 5G | 0 | 6G | 0 | 6G | 0 | 0 | 0 | 9G | 4G | 0 | 10C | 9G | 0 | 2G | 0 | 0 |
| Giant Foxtail | 9G | 4G | 0 | 5G | 2G | 0 | 8G | 4G | 5G | 0 | 0 | 0 | 8G | 0 | 0 | 10C | 8G | 6G | 4G | 2G | 0 |
| Wild Oats | 6G | 2G | 0 | 5G | 2G | 0 | 8G | 5G | 2G | 2G | 2G | 0 | 4G | 0 | 0 | 10C | 7G | 0 | 3G | 0 | 0 |
| Cocklebur | 9G | 5G | 2G | 10G | 9G | 7G | 10G | 10G | 5G | 5G | 5G | 0 | 10G | 9G | 5G | 10C | 10C | 7G | 10G | 9G | 8G |
| Morningglory | 8G | 3C | 0 | 8G | 10G | 8G | 10G | 8G | 5G | 8G | 9G | 3G | 10G | 9G | 6G | 10C | 10C | 9G | 10G | 10G | 3G |
| Teaweed | 6G | 3G | 0 | 5G | 2G | 0 | 8G | 5G | 2G | 5G | 2G | 0 | 6G | 2G | 0 | 10C | 4G | 0 | 7G | 3G | 0 |
| Sicklepod | 8G | 7G | 3G | 8G | 5G | 0 | 9G | 7G | 2G | 0 | 0 | 0 | 6G | 4G | 0 | 10C | 3G | 0 | 4G | 4G | 0 |
| Jimsonweed | 3G | 0 | 0 | 9G | 3G | 2G | 10G | 8G | 3G | 7G | 8G | 5G | 10G | 6G | 3G | 10C | 10C | 4G | 10G | 10G | 5G |
| Velvetleaf | 9G | 9G | 4G | 9G | 6G | 0 | 10G | 9G | 8G | 0 | 5G | 0 | 10G | 8G | 4G | 10C | 9G | 7G | 10G | 9G | 4G |
| Rate g/ha | 250 | 62 | 16 | 250 | 62 | 16 | 250 | 62 | 16 | 1 | 4 | 1 | 250 | 62 | 16 | 250 | 62 | 16 | 250 | 62 | 16 | 4 |
| | | | | | | | PRE-EMERGENCE | | | | | | | | | | | | | | |
| Corn | 7G | 2G | 0 | 0 | 0 | 0 | 9G | 2G | 0 | 0 | 0 | 0 | 9G | 9G | 8G | 10G | 9G | 3G | 10G | 9G | 7G | 2G |
| Wheat | 8G | 6G | 4G | 0 | 0 | 0 | 7G | 0 | 0 | 0 | 0 | 0 | 2G | 0 | 0 | 10G | 9G | 5G | 10G | 9G | 0 | 0 |
| Rice | 10G | 10G | 9G | 8G | 10G | 8G | 10G | 10G | 10G | 9G | 9G | 3G | 10E | 10E | 7G | 10E | 10E | 10E | 10E | 10G | 10E | 5G |
| Soybean | 5G | 2G | 0 | 4G | 4G | 0 | 9G | 6G | 6G | 0 | 0 | 0 | 9G | 8G | 0 | 9G | 8G | 6G | 10G | 10G | 7G | 3G |
| Cotton | 9G | 9G | 2G | 0 | 0 | 0 | 8G | 4G | 4G | 0 | 0 | 0 | 8G | 6G | 2G | 10G | 4G | 2G | 9G | 9G | 4G | 0 |
| Sugar beet | 10G | 8G | 3G | 0 | 0 | 0 | 10G | 7G | 4G | 0 | 0 | 2G | 10G | 6G | 7G | 10G | 6G | 0 | 10G | 10G | 9G | 2G |
| Crabgrass | 7G | 6G | 4G | 8G | 0 | 0 | 9G | 4G | 2G | 2G | 0 | 0 | 9G | 8G | 4G | 10G | 4G | 2G | 8C | 9G | 6G | 0 |
| Johnsongrass | 10G | 9G | 7G | 0 | 0 | 0 | 9G | 3G | 3G | 0 | 2G | 3G | 10C | 8G | 7G | 10C | 9G | 4G | 10E | 10G | 9G | 4G |
| Blackgrass | 10G | 8G | 5G | 0 | 0 | 0 | 10G | 7G | 5G | 0 | 3G | 5G | 8G | 8G | 0 | 8G | 8G | 7G | 10G | 10G | 8G | 4G |
| Barnyardgrass | 9G | 6G | 2G | 5G | 5G | 0 | 10G | 10E | 8G | 0 | 0 | 0 | 5G | 5G | 0 | 10E | 8G | 0 | 10G | 10G | 5G | 4G |
| Nutsedge | 10G | 9G | 5G | 0 | 2G | 0 | 8G | 6G | 3G | 0 | 0 | 0 | 4G | 2G | 0 | 10E | 9G | 0 | 10G | 9G | 4G | 0 |
| Giant Foxtail | 9G | 5G | 2G | — | — | — | — | 5G | 0 | 0 | 0 | 0 | 2G | 2G | 0 | 10E | 10E | 9G | 10G | 6G | 6G | 6G |
| Wild Oats | 9G | 9G | 0 | 0 | 0 | 0 | 9G | 7G | 4G | 0 | 0 | 0 | 3G | 2G | 0 | 10G | 6G | 3G | 10G | 10G | 3G | 2G |
| Cocklebur | 9G | 7G | 7G | 8G | 6G | 6G | 10G | 8G | 6G | 3G | 0 | 0 | 5G | 5G | 0 | 9G | 9G | 3G | 10G | 10G | 9G | 3G |
| Morningglory | 9G | 8G | 2G | 0 | 0 | 0 | 8G | 3G | 0 | 0 | 0 | 0 | 4G | 4G | 2G | 10G | 7G | 3G | 10G | 9G | 6G | 0 |
| Teaweed | 8G | 7G | 4G | 7G | 0 | 6G | 8G | 4G | 6G | 4G | 2G | 0 | 7G | 0 | 2G | 8G | 8G | 4G | 10G | 9G | 3G | 2G |
| Sicklepod | 8G | 5G | 0 | 5G | 0 | 0 | 9G | 2G | 3G | 0 | 0 | 0 | 8G | 8G | 3G | 9G | 8G | 0 | 10G | 6G | 2G | 0 |
| Jimsonweed | 9G | 7G | 3G | 2G | 0 | 0 | 7G | 3G | 0 | 0 | 3G | 3G | 10G | 9G | 2G | 10G | 8G | 6G | 10G | 10G | 8G | 4G |
| Velvetleaf | 9G | 7G | 0 | 0 | 0 | 0 | 8G | 2G | 3G | 0 | 0 | 0 | 10G | 9G | 2G | 9G | 5G | 0 | 10G | 7G | 4G | 2G |

| | Compound 17 | | | Compound 18 | | | Compound 19 | | | Compound 20 | | |
|---|---|---|---|---|---|---|---|---|---|---|---|---|
| Rate g/ha | 62 | 16 | 4 | 250 | 62 | 16 | 4 | 250 | 62 | 16 | 4 | 250 | 62 | 16 | 4 |
| | | | | POST-EMERGENCE | | | | | | | | | |
| Corn | 10G | 9G | 6G | 10G | 7G | 3G | 0 | 10G | 10G | 7G | 2G | 10C | 10C | 10G | 6G |
| Wheat | 3G | 0 | 0 | 6G | 2G | 0 | 0 | 0 | 0 | 0 | 0 | 0 | 2G | 0 | 0 |
| Rice | 10G | 9G | 8G | 10G | 10G | 7G | 3G | 10G | 10G | 9G | 5G | 10C | 10C | 10G | 3G |
| Soybean | 10G | 10C | 10C | 10G | 8G | 7G | 3G | 10G | 10G | 7G | 3G | 10C | 10G | 8G | 8G |

TABLE D-continued

| | | | | | | | | | | | | | | |
|---|---|---|---|---|---|---|---|---|---|---|---|---|---|---|
| Cotton | 9G | 10C | 6G | 2G | 10G | 8G | 7G | 3G | 9G | 8G | 3G | 0 | 10C | 8G | 6G |
| Sugar beet | 10G | 9G | 10G | 7G | 9G | 6G | 2G | 0 | 10C | 10C | 10C | 6G | 10C | 10C | 10C |
| Crabgrass | 4G | 2G | 2G | 0 | 0 | 0 | 0 | 0 | 4G | 0 | 0 | 0 | 10C | 3G | 0 |
| Johnsongrass | 10C | 10G | 9G | 3G | 10C | 3G | 0 | 0 | 9G | 3G | 5G | 0 | 10C | 4G | 0 |
| Blackgrass | 10C | 10C | 8G | 5G | 10C | 3G | 0 | 0 | 10C | 9G | 0 | 0 | 10C | 10C | 5G |
| Barnyardgrass | 8G | 8G | 7G | 4G | 9G | 5C | 0 | 0 | 9G | 5G | 0 | 0 | 10C | 6G | 2G |
| Nutsedge | 7C | 6C | 4G | 0 | 8C | 0 | 0 | 0 | 3G | 3G | 0 | 0 | 5G | 0 | 0 |
| Giant Foxtail | 6G | 5G | 3G | 0 | 5G | 0 | 0 | 0 | 4G | 2G | 0 | 0 | 9G | 3G | 0 |
| Wild Oats | 2G | 0 | 0 | 0 | 7G | 0 | 0 | 0 | 4G | 0 | 0 | 0 | 3G | 0 | 0 |
| Cocklebur | 10C | 10C | 9G | 2G | 10G | 9G | 7G | 3G | 10G | 10G | 7G | 3G | 10C | 10G | 9G |
| Morningglory | 10C | 10C | 7G | 3G | 10G | 8G | 6G | 3G | 8G | 6G | 3G | 0 | 10C | 9G | 6G |
| Teaweed | 7G | 4G | 0 | 0 | 7G | 2G | 0 | 0 | 5G | 2G | 0 | 0 | 7G | 5G | 0 |
| Sicklepod | 7G | 4G | 0 | 0 | 8G | 3G | 0 | 0 | 6G | 3G | 6G | 3G | 10C | 4G | 0 |
| Jimsonweed | 7G | 4G | 0 | 0 | 8G | 4G | 0 | 0 | 9G | 7G | 6G | 2G | 10C | 9G | 8G |
| Velvetleaf | 10G | 9G | 3G | 2G | 10G | 5G | 0 | 0 | 9G | 7G | 4G | 0 | 10C | 10C | 5G |
| Rate g/ha | 250 | 62 | 16 | 4 | 250 | 62 | 16 | 4 | 250 | 62 | 16 | 4 | 250 | 62 | 4 |

PRE-EMERGENCE

| | | | | | | | |
|---|---|---|---|---|---|---|---|
| Corn | 10G | 10G | 9G | 3G | 2G | 0 | 9G | 0 | 10E | 10G | 9G | 5G |
| Wheat | 9G | 8G | 4G | 0 | 2G | 0 | 0 | 0 | 4G | 0 | 0 | 0 |
| Rice | 10E | 10E | 10E | 8G | 9G | 6G | 10E | 3G | 10E | 10E | 9G | 8G |
| Soybean | 9G | 9G | 5G | 3G | 3G | 0 | 9G | 2G | 10G | 9G | 8G | 5G |
| Cotton | 9G | 4G | 0 | 0 | 0 | 0 | 5G | 0 | 10E | 10G | 6G | 0 |
| Sugar beet | 9G | 7G | 3G | 0 | 4G | 0 | 10G | 0 | 10E | 8G | 3G | 7G |
| Crabgrass | 9G | 9G | 3G | 2G | 0 | 2G | 4G | 0 | 9G | 10G | 7G | 2G |
| Johnsongrass | 10C | 9G | 8G | 4G | 6G | 0 | 8G | 3G | 10E | 10G | 10E | 4G |
| Blackgrass | 10E | 10G | 9G | 6G | 9G | 3G | 10G | 2G | 10E | 10E | 7G | 0 |
| Barnyardgrass | 10G | 10G | 9G | 5G | 9G | 5G | 7G | 4G | 10G | 9G | 4G | 0 |
| Nutedge | 9G | 7G | 6G | 0 | 5G | 0 | 5G | 0 | 7G | 8G | 5G | 0 |
| Giant Foxtail | 10G | 10G | 9G | 7G | 5G | 0 | 4G | 0 | 9G | 3G | 0 | 0 |
| Wild Oats | 9G | 5G | 0 | 0 | 3G | 0 | 3G | 0 | 6G | 3G | 0 | 0 |
| Cocklebur | 9G | 8G | 5G | 4G | 3G | 0 | 8G | 4G | 10G | 9G | 5G | 2G |
| Morningglory | 9G | 9G | 6G | 2G | 3G | 0 | 3G | 0 | 10G | 5G | 2G | 0 |
| Teaweed | 9G | 6G | 3G | 3G | 4G | 0 | 2G | 0 | 8G | 4G | 0 | 0 |
| Sicklepod | 9G | 7G | 3G | 0 | 2G | 0 | 2G | 0 | 7G | 3G | 0 | 0 |
| Jimsonweed | 10G | 8G | 8G | 3G | 3G | 0 | 6G | 0 | 10G | 9G | 3G | 0 |
| Velvetleaf | 10G | 8G | 5G | 0 | 2G | 0 | 6G | 0 | 10G | 5G | 0 | 0 |

Test E

Two plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassica napus*). The other pan was planted with seeds of Russian thistle (*Salsola kali*), cleavers (*Galium aparine*), speedwell (*Veronica persica*), kochia (*Kochia scoparia*), shepherd's purse (*Capsella bursa-pastoris*), *Matricaria inodora*, black nightshade (*Solanum nigrum*), wild buckwheat (*Polygonum convolvulus*), and sugar beets (*Beta vulgaris*). The above two pans were treated pre-emergence. At the same time two pans in which the above plant species were growing were treated post-emergence. Plant height at the time of treatment ranged from 1–20 cm depending on plant species.

The compounds applied were diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated. The recorded data are presented in Table E.

TABLE E

| | Compound 13 | | | | | | Compound 14 | | | | | | Compound 16 | | |
|---|---|---|---|---|---|---|---|---|---|---|---|---|---|---|---|
| Rate g/ha | 125 | 64 | 32 | 16 | 8 | 4 | 64 | 32 | 16 | 8 | 4 | 2 | 1 | 125 | 64 | 32 |
| | POST-EMERGENCE | | | | | | | | | | | | | | | |
| wheat | 0 | 0 | 0 | 0 | 0 | 0 | 0 | 0 | 0 | 0 | 0 | 0 | 0 | 1G | 0 | 0 |
| barley | 2G | 0 | 0 | 0 | 0 | 0 | 0 | 0 | 0 | 0 | 0 | 0 | 0 | 4G | 2G | 0 |
| wild oats | 4G | 0 | 0 | 0 | 0 | 0 | 0 | 0 | 0 | 0 | 0 | 0 | 0 | 4G | 4G | 0 |
| cheatgrass | 5G | 2G | 0 | 0 | 0 | 0 | 2G | 0 | 0 | 0 | 0 | 0 | 0 | 4G | 3G | 2G |
| blackgrass | 8G | 8G | 5G | 0 | 0 | 0 | 10C | 9G | 8G | 7G | 5G | 3G | 0 | 8G | 8G | 7G |
| annual bluegrass | 10C | 8G | 7G | 4G | 4G | 2G | 10C | 8G | 4G | 4G | 3G | 0 | 0 | 8G | 6G | 6G |
| green foxtail | 10C | 8G | 8G | 6G | 5G | 4G | 5G | 4G | 4G | 3G | 3G | 0 | 0 | 7G | 7G | 5G |
| Italian ryegrass | 3G | 0 | 0 | 0 | 0 | 0 | 0 | 0 | 0 | 0 | 0 | 0 | 0 | 7G | 4G | 0 |
| rapeseed | 10C | 10C | 9G | 8G | 8G | 8G | 10C | 10C | 10C | 9G | 8G | 7G | 6G | 9G | 10C | 10C |
| *Matricaria inodora* | 9G | 10C | 9G | 9G | 7G | 6G | 2G | 2G | 0 | 0 | 0 | 0 | 0 | 10C | 10C | 9G |
| Galium | 9G | 10C | 9G | 8G | 0 | 0 | 0 | 0 | 0 | 0 | 0 | 0 | 0 | 10C | — | 10C |
| Russian thistle | 5G | 5G | 5G | 5G | 0 | 0 | 5G | 5G | 4G | 3G | 3G | 3G | 2G | 10C | 10C | 10C |
| shepherd's purse | 10C | 10C | 10C | 10C | 10C | 10C | 10C | 7G | 8G | 5G | 7G | 5G | 3G | 7G | 8G | 7G |
| kochia | 10C | 10C | 8G | 8G | 5G | 3G | 10C | 6G | 5G | 0 | 0 | 0 | 0 | 8G | 9G | 8G |
| black nightshade | 8G | 8G | 2G | 0 | 0 | 0 | 2G | 0 | 0 | 0 | 0 | 0 | 0 | 7G | 9G | 7G |
| speedwell | 4G | 0 | 0 | 0 | 0 | 0 | 2G | 0 | 0 | 0 | 0 | 0 | 0 | 0 | 0 | 0 |
| wild buckwheat | 0 | 0 | 0 | 0 | 0 | 0 | 0 | 0 | 0 | 0 | 0 | 0 | 0 | 0 | 0 | 0 |
| sugar beets | 10C | 10C | 10C | 10C | 9G | 9G | 8G | 8G | 8G | 8G | 7G | 7G | 6G | 9G | 10C | 8G |
| | PRE-EMERGENCE | | | | | | | | | | | | | | | |
| wheat | 0 | 0 | 0 | 0 | 0 | 0 | 3G | 1G | 0 | 0 | 0 | 0 | 0 | 0 | 0 | 0 |
| barley | 2G | 2G | 0 | 0 | 0 | 0 | 2G | 2G | 0 | 0 | 0 | 0 | 0 | 1G | 0 | 0 |
| wild oats | 7G | 4G | 0 | 0 | 0 | 0 | 50 | 4G | 2G | 2G | 0 | 0 | 0 | 5G | 4G | 2G |
| cheatgrass | 6G | 3G | 0 | 0 | 0 | 0 | 6G | 5G | 0 | 0 | 0 | 0 | 0 | 6G | 5G | 4G |
| blackgrass | 7G | 8G | 5G | 0 | 0 | 0 | 8G | 7G | 7G | 2G | 2G | 0 | 0 | 7G | 7G | 7G |
| annual bluegrass | 6G | 7G | 4G | 2G | 0 | 0 | 8G | 7G | 6G | 3G | 2G | 0 | 0 | 7G | 7G | 6G |
| green foxtail | 7G | 6G | 4G | 0 | 0 | 0 | 4G | 5G | 2G | 0 | 0 | 0 | 0 | 6G | 7G | 4G |
| Italian ryegrass | 0 | 0 | 0 | 0 | 0 | 0 | 3G | 0 | 0 | 0 | 0 | 0 | 0 | 4G | 3G | 2G |
| rapeseed | 9G | 8G | 8G | 6G | 4G | 4G | 7G | 6G | 5G | 3G | 0 | 0 | 0 | 10C | 10C | 10C |
| *Matricaria inodora* | 10C | 7G | 3G | 5G | 0 | 0 | 8G | 6G | 5G | 2G | 2G | 0 | 0 | 9G | 9G | 9G |
| Galium | 8G | 5G | 5G | 0 | 0 | 0 | 5G | 0 | 0 | 0 | 0 | 0 | 0 | 0 | 0 | — |
| Russian thistle | 6G | 3G | 0 | 0 | 0 | 0 | 2G | 2G | 0 | 0 | 0 | 0 | 0 | 0 | 0 | 0 |
| shepherd's purse | 10C | 10C | 9G | 9G | 5G | 0 | 9G | 8G | 6G | 5G | 2G | 0 | 0 | 10C | 10C | 9G |
| kochia | 5G | 0 | 0 | 0 | 0 | 0 | 9G | 7G | 5G | 0 | 0 | 0 | 0 | 8G | 8G | 7G |
| black nightshade | 8G | 8G | 4G | 0 | 0 | 0 | 8G | 2G | 0 | 0 | 0 | 0 | 0 | 8G,7C | 8G,5C | 7G,3C |
| speedwell | 0 | 0 | 0 | 0 | 0 | 0 | 7G | 0 | 0 | 0 | 0 | 0 | 0 | 7G | 6G | 3G |
| wild buckwheat | 0 | 0 | 0 | 0 | 0 | 0 | 7G | 0 | 0 | 0 | 0 | 0 | 0 | 8G,3C | 8G | 8G |
| sugar beets | 10C | 10C | 8G | 8G | 7G | 7G | 10C | 9G | 7G | 5G | 5G | 2G | 2G | 10C | 9G | 9G |

| | Compound 16 | | | Compound 17 | | | | | | | Compound 20 | | | | | |
|---|---|---|---|---|---|---|---|---|---|---|---|---|---|---|---|---|
| Rate g/ha | 16 | 4 | 1 | 125 | 64 | 32 | 16 | 8 | 4 | 1 | 125 | 64 | 32 | 16 | 4 | 1 |
| | POST-EMERGENCE | | | | | | | | | | | | | | | |
| wheat | 0 | 0 | 0 | 4G | 4G | 4G | 4G | 4G | 3G | 0 | 3G | 0 | 0 | 0 | 0 | 0 |
| barley | 0 | 0 | 0 | 7G | 7G | 7G | 6G | 5G | 3G | 0 | 5G | 3G | 3G | 0 | 0 | 0 |
| wild oats | 0 | 0 | 0 | 4G | 3G | 3G | 0 | 0 | 0 | 0 | 5G | 2G | 2G | 0 | 0 | 0 |
| cheatgrass | 2G | 1G | 0 | 6G | 7G | 7G | 7G | 6G | 5G | 3G | 8G | 7G | 5G | 3G | 0 | 0 |
| blackgrass | 6G | 4G | 0 | 9G | 9G | 9G | 9G | 9G | 8G | 6G | 10C | 10C | 10C | 9G | 6G | 4G |
| annual bluegrass | 5G | 3G | 2G | 9G | 9G | 8G | 8G | 8G | 7G | 5G | 9G | 7G | 7G | 6G | 0 | 0 |
| green foxtail | 3G | 3G | 0 | 7G | 7G | 7G | 7G | 6G | 6G | 4G | 8G | 7G | 7G | 6G | 4G | 2G |
| Italian ryegrass | 0 | 0 | 0 | 8G | 8G | 7G | 7G | 7G | 6G | 2G | 9G | 9G | 8G | 5G | 3G | 0 |
| rapeseed | 9G | 9G | 8G | 10C | 10C | 10C | 10C | 10C | 10C | 8G | 9G | 10C | 10C | 10C | 9G | 8G |
| *Matricaria inodora* | 10C | 7G | 5G | 10C | 9G | 8G | 6G | 3G,5C | 3G | 0 | 10C | 10C | 10C | 9G | 6G | 3G |
| Galium | — | — | — | — | — | — | 5G | — | 2G | 0 | — | 10C | 10C | — | — | — |
| Russian thistle | 5G | 0 | 0 | 8G | 8G | 8G | 7G | 7G | 0 | 0 | 10C | 10C | 10C | 10C | 7G | 5G |
| shepherd's purse | 4G | 0 | 0 | 9G | 9G | 9G | 9G | 6G | 5G | 5G | 10C | 10C | 10C | 10C | 10C | 8G |
| kochia | 6G | 6G | 4G | 0 | 0 | 0 | 0 | 0 | 0 | 0 | 8G | 6G | 4G | 2G | 0 | 0 |
| black nightshade | 4G | 2G | 1G | 3G | 1G | 1G | 0 | 0 | 0 | 0 | 10C | 10C | 9G | 7G | 7G | 3G |
| speedwell | 0 | 0 | 0 | 3G | 2G | 2G | 2G | 2G | 0 | 0 | 10C | 10C | 10C | 10C | 7G | 5G |
| wild buckwheat | 0 | 0 | 0 | 3G | 0 | 0 | 0 | 0 | 0 | 0 | 10C | 10C | 8G | 4G | 2G | 0 |
| sugar beets | 9G | 7G | 4G | 9G | 7G | 7G | 4G | 1G | 0 | 0 | 10C | 10C | 10C | 10C | 8G | 7G |

TABLE E-continued

| | | | | PRE-EMERGENCE | | | | | | | | | | | |
|---|---|---|---|---|---|---|---|---|---|---|---|---|---|---|---|
| wheat | 0 | 0 | 0 | 7G | 7G | 6G | 7G | 7G | 2G | 0 | 4G | 3G | 2G | 0 | 0 | 0 |
| barley | 0 | 0 | 0 | 8G | 8G | 6G | 5G | 5G | 3G | 1G | 6G | 3G | 3G | 0 | 0 | 0 |
| wild oats | 2G | 2G | 0 | 8G,3C | 7G,3C | 7G | 4G | 6G | 3G | 0 | 7G | 6G | 5G | 3G | 0 | 0 |
| cheatgrass | 3G | 3G | 1G | 9G,5C | 9G | 9G | 9G | 9G | 8G | 5G | 9G | 8G | 7G | 6G | 4G | 4G |
| blackgrass | 5G | 3G | 1G | 10C | 10C | 9G,5C | 9G,5C | 9G,5C | 8G | 7G | 9G,7C | 9G | 8G | 8G | 7G | 4G |
| annual bluegrass | 5G | 3G | 0 | 9G,7C | 9G,5C | 8G | 8G | 8G | 8G | 5G | 9G | 9G | 8G | 7G | 5G | 5G |
| green foxtail | 3G | 1G | 0 | 9G,5C | 9G | 9G | 8G | 8G | 8G | 3G | 9G | 7G | 5G | 3G | 2G | 2G |
| Italian ryegrass | 0 | 0 | 0 | 9G | 9G | 9G | 9G | 9G | 8G | 4G | 9G | 9G | 9G | 5G | 3G | 2G |
| rapeseed | 9G | 9G | 6G | 10C | 10C | 9G | 9G | 9G | 9G | 8G | 10C | 9G | 9G | 9G | 8G | 7G |
| *Matricaria inodora* | 9G | 8G | 6G | 9G | 9G | 9G | 9G | 9G | 9G | 8G | 9G | 9G | 9G | 9G | 8G | 8G |
| Galium | — | — | — | — | — | — | 5G | — | 0 | — | — | — | — | — | — | — |
| Russian thistle | 0 | 0 | 0 | 5G | 5G | 5G | 4G | 3G | 2G | 0 | 6G | 4G,5C | 4G,5C | 4G | 0 | 0 |
| shepherd's purse | 9G | 9G | 1G | 10C | 9G | 10C | 9G | 9G | 9G | 8G | 10C | 9G | 9G | 9G | 9G | 7G |
| kochia | 7G | 2G | 0 | 9G | 6G | 6G | 6G | 4G | 4G | 3G | 9G | 9G | 9G | 8G | 5G | 3G |
| black nightshade | 8G,3C | 6G | 2G | 6G | 5G | 3G | 3G | 0 | 0 | 0 | 8G,7C | 8G,5C | 8G | 7G | 6G | 0 |
| speedwell | 3G | 0 | 0 | 10C | 10C | 10C | 9G | 8G | 6G | 5G | 10C | 10C | 9G | 9G | 9G | 7G |
| wild buckwheat | 8G | 7G | 2G | 9G | 9G,3C | 9G | 9G | 8G | 6G | 5G | 8G,5C | 8G,5C | 8G | 8G | 9G | 3G |
| sugar beets | 9G | 10C | 7G | 9G | 9G | 9G | 9G | 9G | 8G | 7G | 10C | 10C | 10C | 10C | 10C | 8G |

What is claimed is:

1. A compound of the formula:

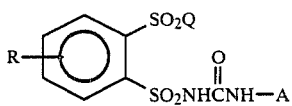

wherein

Q is NR$_1$R$_2$,

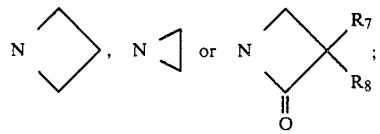

R is H, Cl Br, F, OCH$_3$, CH$_3$ or CF$_3$;
R$_1$ is C(O)R$_3$, C(O)NR$_4$R$_5$, CO$_2$R$_6$, C(O)NHR$_9$ or CF$_2$H;
R$_2$ is H or C$_1$-C$_3$ alkyl;
R$_3$ is C$_1$-C$_4$ alkyl, CF$_3$ or phenyl optionally substituted with Cl, CH$_3$, CF$_3$, NO$_2$ or OCH$_3$;
R$_4$ is H, C$_1$-C$_4$ alkyl or phenyl optionally substituted with Cl, CH$_3$, CF$_3$, NO$_2$ or OCH$_3$;
R$_5$ is H or C$_1$-C$_4$ alkyl;
R$_4$ and R$_5$ may be taken together to be —(CH$_2$)$_4$—, —(CH$_2$)$_5$— or —CH$_2$CH$_2$OCH$_2$CH$_2$—;
R$_6$ is C$_1$-C$_4$ alkyl;
R$_7$ and R$_8$ are independently H or CH$_3$;
R$_9$ is A-1;
A is

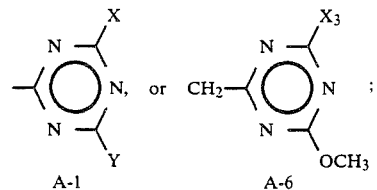

X is CH$_3$, CH$_2$CH$_3$, OCH$_3$, OCH$_2$CH$_3$ or CF$_3$;
Y is H, NHCH$_3$N(CH$_3$)$_2$, CH$_3$, CH$_2$CH$_3$, CF$_3$, OCH$_3$, OCH$_2$CH$_3$, CH$_2$F, CH$_2$OCH$_3$, CH$_2$OCH$_2$CH$_3$, OCH$_2$CH$_2$OCH$_3$, SCH$_3$, SCH$_2$CH$_3$, OCH$_2$CF$_3$, OCH$_2$CH$_2$F, OCH$_2$CH$_2$Br, OCH$_2$CH$_2$Cl, CH(OCH$_3$)$_2$, CH(OC$_2$H$_5$)$_2$,

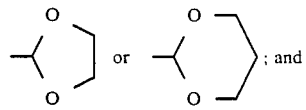

X$_3$ is CH$_3$ or OCH$_3$;

and their agriculturally suitable salts; provided that
when R$_1$ is CONHR$_9$, then A must be A-1 and the values of X, Y and Z must be identical for both A and R$_9$.

2. A compound of claim 1 where R is H, A is A-1, X is CH$_3$, CH$_2$CH$_3$, OCH$_3$, OCH$_2$CH$_3$ or CF$_3$ and Y is CH$_3$, CH$_2$CH$_3$, CF$_3$, OCH$_2$CH$_3$, CH$_2$OCH$_3$ or CH(OCH$_3$)$_2$.

3. A compound of claim 2 where Q is NR$_1$R$_2$ or

and R$_2$ is H or CH$_3$.

4. A compound of claim 3 where Q is NR$_1$R$_2$ or

R$_2$ is H, X is CH$_3$ or OCH$_3$ and Y is CH$_3$, CH$_2$CH$_3$, OCH$_3$, OCH$_2$CH$_3$ or CH$_2$OCH$_3$.

5. A compound of claim 1 where R$_1$ is C(O)NHR$_9$.

6. A compound of claim 1 where Q is

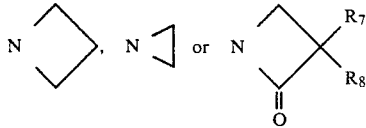

7. The compound of claim 1 which is 2-(azetidin-1-ylsulfonyl)-N-[(4,6-dimethoxy-1,3,5-triazin-2-yl)aminocarbonyl]benzenesulfonamide.

8. The compound of claim 1 which is 2-(azetidin-1-ylsulfonyl)-N-[(4-methoxy-6-methyl-1,3,5-triazin-2-yl)aminocarbonyl]benzenesulfonamide.

9. A composition suitable for controlling the growth of undesired vegetation which comprises an effective amount of a compound of claim 1 and at least one of the following: surfactant, solid or liquid diluent.

10. A composition suitable for controlling the growth of undesired vegetation which comprises an effective amount of a compound of claim 2 and at least one of the following: surfactant, solid or liquid diluent.

11. A composition suitable for controlling the growth of undesired vegetation which comprises an effective amount of a compound of claim 7 and at least one of the following: surfactant, solid or liquid diluent.

12. A composition suitable for controlling the growth of undesired vegetation which comprises an effective amount of a compound of claim 8 and at least one of the following: surfactant, solid or liquid diluent.

13. A method for controlling the growth of undesired vegetation which comprises applying to the locus to be protected an effective amount of a compound of claim 1.

14. A method for controlling the growth of undesired vegetation which comprises applying to the locus to be protected an effective amount of a compound of claim 2.

15. A method for controlling the growth of undesired vegetation which comprises applying to the locus to be protected an effective amount of a compound of claim 7.

16. A method for controlling the growth of undesired vegetation which comprises applying to the locus to be protected an effective amount of a compound of claim 8.

* * * * *